(12) United States Patent
Ask et al.

(10) Patent No.: US 10,947,571 B2
(45) Date of Patent: Mar. 16, 2021

(54) METHOD FOR PRODUCING LACTIC ACID IN RECOMBINANT YEAST CELL CULTURE

(71) Applicant: Syconium Lactic Acid GmbH, Vienna (AT)

(72) Inventors: Magnus Ask, Malmö (SE); Rakesh Koppram, Gothenburg (SE); Diethard Mattanovich, Vienna (AT); Michael Sauer, Vienna (AT)

(73) Assignee: SYCONIUM LACTIC ACID GMBH, Vienna (AT)

( * ) Notice: Subject to any disclaimer, the term of this patent is extended or adjusted under 35 U.S.C. 154(b) by 0 days.

(21) Appl. No.: 16/094,186

(22) PCT Filed: Apr. 14, 2017

(86) PCT No.: PCT/EP2017/059046
§ 371 (c)(1),
(2) Date: Oct. 16, 2018

(87) PCT Pub. No.: WO2017/182403
PCT Pub. Date: Oct. 26, 2017

(65) Prior Publication Data
US 2019/0127766 A1 May 2, 2019

(30) Foreign Application Priority Data
Apr. 18, 2016 (EP) ..................................... 16165772

(51) Int. Cl.
*C12P 7/56* (2006.01)
*C12N 1/18* (2006.01)
*C12N 15/52* (2006.01)
*C07K 14/395* (2006.01)
*C12N 9/04* (2006.01)
*C12N 9/88* (2006.01)

(52) U.S. Cl.
CPC .............. *C12P 7/56* (2013.01); *C07K 14/395* (2013.01); *C12N 1/18* (2013.01); *C12N 9/0006* (2013.01); *C12N 9/88* (2013.01); *C12N 15/52* (2013.01); *C12Y 101/01027* (2013.01); *C12Y 401/01001* (2013.01)

(58) Field of Classification Search
None
See application file for complete search history.

(56) References Cited

U.S. PATENT DOCUMENTS

| 2015/0104543 A1* | 4/2015 | Winkler | C12P 7/46 426/61 |
| 2016/0024539 A1* | 1/2016 | Song | C12P 7/40 435/131 |

FOREIGN PATENT DOCUMENTS

| WO | 2004099425 A2 | 11/2004 |
| WO | 2009144013 A1 | 3/2009 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Skory. J Ind Microbiol Biotechnol (2003) 30: 22-27 (Year: 2003).*
Lee et al. Biotechnol Bioeng. Apr. 2015;112(4):751-8. Epub Jan. 16, 2015. (Year: 2015).*
Weinhandl et al. Carbon source dependent promoters in yeasts. Microb Cell Fact 13, 5 (2014) (Year: 2014).*
International Written Opinion for International Application No. PCT/EP2017/059046, dated Jul. 7, 2017, 7 pages.
International Search Report for International Application No. PCT/EP2017/059046, dated Jul. 7, 2017, 7 pages.
International Preliminary Report on Patentability for International Application No. PCT/EP2017/059046, dated Oct. 23, 2018, 8 pages.
European Search Report for European Application No. 16165772.1, dated Oct. 14, 2016, 9 pages.
Partial European Search Report for European Application No. 16165772.1, dated Oct. 14, 2016, 6 pages.
Partial International Search Report for International Application No. PCT/EP2017/059046, dated Jul. 13, 2017, 11 pages.
Branduardi, Paola et al., "Lactate production yield from engineered yeasts is dependent from the host background, the lactate dehydrogenase source and the lactate export," Microbial Cell Factories, 2006, 5:4, 12 pages.
Cakar, Petek Z. et al., Evolutionary engineering of *Saccharomyces cerevisiae* for improved industrially important properties, FEMS Yeast Res, 12 (2012) 171-182.
Engler, Carola et al., A One Pot, One Step, Precision Cloning Method with High Throughput Capability, PLoS ONE, 3(11) e3647 (2008).
Miller et al., Industrial Production of Lactic Acid, Elsevier, pp. 179-188 (2011).
Ozcan, Sabire et al., "Three Different Regulatory Mechanisms Enable Yeast Hexose Transporter (HXT) Genes to Be Induced by Different Levels of Glucose," Mol Cell Biol, 15(3):1564-1572 (1995).
Sauer, Michael et al., Biotechnology and Genetic Engineering Reviews, "16 years research on lactic acid production with yeast—ready for the market?" 27(1):229-256 (2010).

(Continued)

*Primary Examiner* — Christian L Fronda
(74) *Attorney, Agent, or Firm* — Loza & Loza, LLP; Michael F. Fedrick

(57) ABSTRACT

The present invention provides a method for producing lactic acid in a recombinant yeast cell culture using glucose as carbon source comprising a first, seed fermentation stage to produce biomass wherein the yeast is cultivated in a culture medium at a pH of 5 to 7, followed by a second, a production fermentation stage with biomass from the seed fermentation to produce lactic acid, wherein the yeast is cultivated in a culture medium at low p H using a yeast strain that is engineered to have lactate dehydrogenase (LDH) activity and optionally has decreased or knocked-out pyruvate decarboxylase (PDC) activity.

14 Claims, 2 Drawing Sheets

Figure 1:
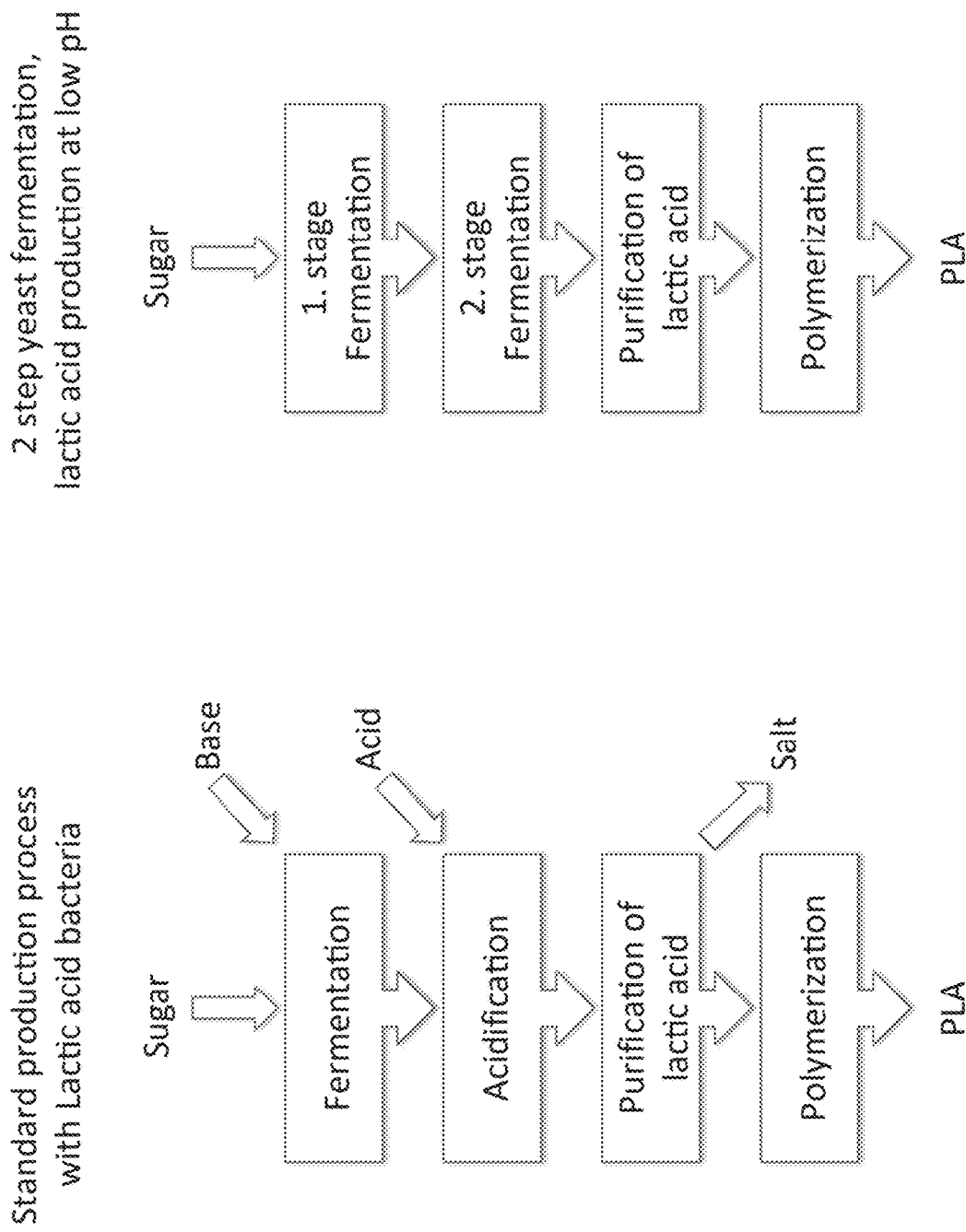

Specification includes a Sequence Listing.

(56) References Cited

OTHER PUBLICATIONS

Sauer, Michael et al., Microbial production of organic acids: expanding the markets, Trends in Biotechnology, vol. 26, No. 2, pp. 100-108 (2008).
Sauer, Uwe, Institute of Biotechnology, "Evolutionary Engineering of Industrially Important Microbial Phenotypes," Adv Biochem Eng Biotechnol, vol. 73, pp. 130-166 (2001).
Storchova, Zuzana, "Group Maintenance of Genome Stability, Ploidy changes and genome stability in yeast," Yeast, vol. 31, No. 11, pp. 421-430 (2014).

\* cited by examiner

SEQUENCE LISTING

```
<160> NUMBER OF SEQ ID NOS: 83

<210> SEQ ID NO 1
<211> LENGTH: 320
<212> TYPE: PRT
<213> ORGANISM: Artificial Sequence
<220> FEATURE:
<223> OTHER INFORMATION: LDH gene

<400> SEQUENCE: 1

Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
```

```
                     65                  70                  75                  80
                Thr Ala Gly Ala Pro Gln Lys Pro Gly Glu Ser Arg Leu Asp Leu Val
                                 85                  90                  95
                Asn Lys Asn Leu Asn Ile Leu Ser Ser Ile Val Lys Pro Val Val Asp
                                100                 105                 110
                Ser Gly Phe Asp Gly Ile Phe Leu Val Ala Ala Asn Pro Val Asp Ile
                                115                 120                 125
                Leu Thr Tyr Ala Thr Trp Lys Phe Ser Gly Phe Pro Lys Asp Arg Val
                    130                 135                 140
                Ile Gly Ser Gly Thr Ser Leu Asp Ser Arg Leu Arg Val Ala Leu
                145                 150                 155                 160
                Gly Lys Gln Phe Asn Val Asp Pro Arg Ser Val Asp Ala Tyr Ile Met
                                165                 170                 175
                Gly Glu His Gly Asp Ser Glu Phe Ala Ala Tyr Ser Thr Ala Thr Ile
                                180                 185                 190
                Gly Thr Arg Pro Val Arg Asp Val Ala Lys Glu Gln Gly Val Ser Asp
                            195                 200                 205
                Glu Asp Leu Ala Lys Leu Glu Asp Gly Val Arg Asn Lys Ala Tyr Asp
                    210                 215                 220
                Ile Ile Asn Leu Lys Gly Ala Thr Phe Tyr Gly Ile Gly Thr Ala Leu
                225                 230                 235                 240
                Met Arg Ile Ser Lys Ala Ile Leu Arg Asp Glu Asn Ala Val Leu Pro
                                245                 250                 255
                Val Gly Ala Tyr Met Asp Gly Gln Tyr Gly Leu Asn Asp Ile Tyr Ile
                                260                 265                 270
                Gly Thr Pro Ala Val Ile Gly Gly Thr Gly Leu Lys Gln Ile Ile Glu
                            275                 280                 285
                Ser Pro Leu Ser Ala Asp Glu Leu Lys Lys Met Gln Asp Ser Ala Ala
                        290                 295                 300
                Thr Leu Lys Lys Val Leu Asn Asp Gly Leu Ala Glu Leu Glu Asn Lys
                305                 310                 315                 320

<210> SEQ ID NO 2
<211> LENGTH: 54
<212> TYPE: DNA
<213> ORGANISM: Artificial Sequence
<220> FEATURE:
<223> OTHER INFORMATION: Primer

<400> SEQUENCE: 2
caaaatgcat aacctatgca tttaaaagat tatgtatgct cttctgactt ttcg         54

<210> SEQ ID NO 3
<211> LENGTH: 56
<212> TYPE: DNA
<213> ORGANISM: Artificial Sequence
<220> FEATURE:
<223> OTHER INFORMATION: Primer

<400> SEQUENCE: 3
taagtgacag tgcagtaata atatgaacca atttattttt cgttacataa aaatgc       56

<210> SEQ ID NO 4
<211> LENGTH: 49
<212> TYPE: DNA
<213> ORGANISM: Artificial Sequence
<220> FEATURE:
<223> OTHER INFORMATION: Primer
```

<400> SEQUENCE: 4 cattattta attttttttc tattactgtc gctaacacct gtatggttg    49

<210> SEQ ID NO 5
<211> LENGTH: 49
<212> TYPE: DNA
<213> ORGANISM: Artificial Sequence
<220> FEATURE:
<223> OTHER INFORMATION: Primer

<400> SEQUENCE: 5
gcatattaat agtatacaac aaaaacaaag gaaaaaaga aatgaaatc    49

<210> SEQ ID NO 6
<211> LENGTH: 57
<212> TYPE: DNA
<213> ORGANISM: Artificial Sequence
<220> FEATURE:
<223> OTHER INFORMATION: Primer

<400> SEQUENCE: 6
ctatgtactt ggcaatagat gagcatttca atgaaggaaa cgcctgagtc agttatg    57

<210> SEQ ID NO 7
<211> LENGTH: 58
<212> TYPE: DNA
<213> ORGANISM: Artificial Sequence
<220> FEATURE:
<223> OTHER INFORMATION: Primer

<400> SEQUENCE: 7
gggcggcgtc ccctgttttt ctgctttggc tcatctcttt ggctccgacg gacgaaag    58

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
aaggctcttt cactctcctt gc    22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ttagcggcgt cagcaatagt gg    22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ccactattgc tgacgccgct aa    22

<210> SEQ ID NO 11
<211> LENGTH: 22

```
<212> TYPE: DNA
<213> ORGANISM: Artificial Sequence
<220> FEATURE:
<223> OTHER INFORMATION: Primer

<400> SEQUENCE: 11
tcgctaacac ctgtatggtt gc                                              22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cttgacatca tgtctagaag c                                               21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ttctagacat gatgtcaagg c                                               21

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
actaagtgac aaagaactac gc                                              22

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tacagtcggt aatttctttc tgg                                             23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ggatcaaatc agccgactca acg                                             23

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
```
cgttgagtcg gctgatttga tcc                                              23

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
taaagctgta agctagacca cc                                               22

<210> SEQ ID NO 19
<211> LENGTH: 20
<212> TYPE: DNA
<213> ORGANISM: Artificial Sequence
<220> FEATURE:
<223> OTHER INFORMATION: gRNA

<400> SEQUENCE: 19
gatacgagcg taaccatcag                                                  20

<210> SEQ ID NO 20
<211> LENGTH: 20
<212> TYPE: DNA
<213> ORGANISM: Artificial Sequence
<220> FEATURE:
<223> OTHER INFORMATION: gRNA

<400> SEQUENCE: 20
tgaagtcaaa ggtatgagat                                                  20

<210> SEQ ID NO 21
<211> LENGTH: 20
<212> TYPE: DNA
<213> ORGANISM: Artificial Sequence
<220> FEATURE:
<223> OTHER INFORMATION: gRNA

<400> SEQUENCE: 21
gtaaccatcg gcggcatagg                                                  20

<210> SEQ ID NO 22
<211> LENGTH: 51
<212> TYPE: DNA
<213> ORGANISM: Artificial Sequence
<220> FEATURE:
<223> OTHER INFORMATION: Primer

<400> SEQUENCE: 22
catgcgtatc ctgatgagtc cgtgaggacg aaacgagtaa gctcgtcgat a               51

<210> SEQ ID NO 23
<211> LENGTH: 60
<212> TYPE: DNA
<213> ORGANISM: Artificial Sequence
<220> FEATURE:
<223> OTHER INFORMATION: Primer

<400> SEQUENCE: 23
aaacgagtaa gctcgtcgat acgagcgtaa ccatcaggtt ttagagctag aaatagcaag      60

<210> SEQ ID NO 24
<211> LENGTH: 51
<212> TYPE: DNA
<213> ORGANISM: Artificial Sequence

```
<220> FEATURE:
<223> OTHER INFORMATION: Primer

<400> SEQUENCE: 24
catgacttca ctgatgagtc cgtgaggacg aaacgagtaa gctcgtctga a            51

<210> SEQ ID NO 25
<211> LENGTH: 60
<212> TYPE: DNA
<213> ORGANISM: Artificial Sequence
<220> FEATURE:
<223> OTHER INFORMATION: Primer

<400> SEQUENCE: 25
aaacgagtaa gctcgtctga agtcaaaggt atgagatgtt ttagagctag aaatagcaag   60

<210> SEQ ID NO 26
<211> LENGTH: 51
<212> TYPE: DNA
<213> ORGANISM: Artificial Sequence
<220> FEATURE:
<223> OTHER INFORMATION: Primer

<400> SEQUENCE: 26
catgggttac ctgatgagtc cgtgaggacg aaacgagtaa gctcgtcgta a            51

<210> SEQ ID NO 27
<211> LENGTH: 60
<212> TYPE: DNA
<213> ORGANISM: Artificial Sequence
<220> FEATURE:
<223> OTHER INFORMATION: Primer

<400> SEQUENCE: 27
aaacgagtaa gctcgtcgta accatcggcg gcatagggtt ttagagctag aaatagcaag   60

<210> SEQ ID NO 28
<211> LENGTH: 60
<212> TYPE: DNA
<213> ORGANISM: Artificial Sequence
<220> FEATURE:
<223> OTHER INFORMATION: Primer

<400> SEQUENCE: 28
gttttagagc tagaaatagc aagttaaaat aaggctagtc cgttatcaac ttgaaaaagt   60

<210> SEQ ID NO 29
<211> LENGTH: 60
<212> TYPE: DNA
<213> ORGANISM: Artificial Sequence
<220> FEATURE:
<223> OTHER INFORMATION: Primer

<400> SEQUENCE: 29
cgccatgccg aagcatgttg cccagccggc gccagcgagg aggctgggac catgccggcc   60

<210> SEQ ID NO 30
<211> LENGTH: 60
<212> TYPE: DNA
<213> ORGANISM: Artificial Sequence
<220> FEATURE:
<223> OTHER INFORMATION: Primer

<400> SEQUENCE: 30
aggctgggac catgccggcc aaaagcaccg actcggtgcc acttttttcaa gttgataacg   60
```

<210> SEQ ID NO 31
<211> LENGTH: 51
<212> TYPE: DNA
<213> ORGANISM: Artificial Sequence
<220> FEATURE:
<223> OTHER INFORMATION: Primer

<400> SEQUENCE: 31
aagcagtcca aagctgtccc attcgccatg ccgaagcatg ttgcccagcc g          51

<210> SEQ ID NO 32
<211> LENGTH: 230
<212> TYPE: DNA
<213> ORGANISM: Artificial Sequence
<220> FEATURE:
<223> OTHER INFORMATION: gRNA construct

<400> SEQUENCE: 32
catgcgtatc ctgatgagtc cgtgaggacg aaacgagtaa gctcgtcgat acgagcgtaa      60
ccatcaggtt ttagagctag aaatagcaag ttaaaataag gctagtccgt tatcaacttg     120
aaaaagtggc accgagtcgg tgcttttggc cggcatggtc ccagcctcct cgctggcgcc     180
ggctgggcaa catgcttcgg catggcgaat gggacagctt tggactgctt               230

<210> SEQ ID NO 33
<211> LENGTH: 230
<212> TYPE: DNA
<213> ORGANISM: Artificial Sequence
<220> FEATURE:
<223> OTHER INFORMATION: gRNA construct

<400> SEQUENCE: 33
catgacttca ctgatgagtc cgtgaggacg aaacgagtaa gctcgtctga agtcaaaggt      60
atgagatgtt ttagagctag aaatagcaag ttaaaataag gctagtccgt tatcaacttg     120
aaaaagtggc accgagtcgg tgcttttggc cggcatggtc ccagcctcct cgctggcgcc     180
ggctgggcaa catgcttcgg catggcgaat gggacagctt tggactgctt               230

<210> SEQ ID NO 34
<211> LENGTH: 230
<212> TYPE: DNA
<213> ORGANISM: Artificial Sequence
<220> FEATURE:
<223> OTHER INFORMATION: gRNA construct

<400> SEQUENCE: 34
catgggttac ctgatgagtc cgtgaggacg aaacgagtaa gctcgtcgta accatcggcg      60
gcatagggtt ttagagctag aaatagcaag ttaaaataag gctagtccgt tatcaacttg     120
aaaaagtggc accgagtcgg tgcttttggc cggcatggtc ccagcctcct cgctggcgcc     180
ggctgggcaa catgcttcgg catggcgaat gggacagctt tggactgctt               230

<210> SEQ ID NO 35
<211> LENGTH: 180
<212> TYPE: DNA
<213> ORGANISM: Artificial Sequence
<220> FEATURE:
<223> OTHER INFORMATION: dsDNA oligo

<400> SEQUENCE: 35
aacttgtcct tgttggacaa gatctacgaa gttgaaggta tgagatgggc tggtaacgcc      60
aacgaattga acgctgctta cgctgctgat tgaatggtta cgctcgatca agggtatgtc     120

```
ttgtatcatc accaccttcg gtgtcggtga attgtctgct ttgaacggta ttgccggttc    180
```

```
<210> SEQ ID NO 36
<211> LENGTH: 180
<212> TYPE: DNA
<213> ORGANISM: Artificial Sequence
<220> FEATURE:
<223> OTHER INFORMATION: dsDNA oligo

<400> SEQUENCE: 36
tgtctgccaa catttctgaa accactgcca tgatcactga tattgctaac gctccagctg    60
aaattgacag atgtatcaga aacacctact agacactacc caagaccagt ctacttgggt   120
ttgccagcta acttggttga cttgaacgtc ccagccaagt tattggaaac tccaattgac   180

<210> SEQ ID NO 37
<211> LENGTH: 180
<212> TYPE: DNA
<213> ORGANISM: Artificial Sequence
<220> FEATURE:
<223> OTHER INFORMATION: dsDNA oligo

<400> SEQUENCE: 37
caggcgactt caacttgtcc ctattggaca agatttacga ggtagatgga ttgagatggg    60
ctggtaatgc aaatgagctg aacgacgcct attgaatgcc gccgatggta cgcacgcatc   120
aagggtttat ctgtgctggt aactactttt ggcgtaggtg aattatccgc cttgaatggt   180

<210> SEQ ID NO 38
<211> LENGTH: 20
<212> TYPE: DNA
<213> ORGANISM: Artificial Sequence
<220> FEATURE:
<223> OTHER INFORMATION: gRNA

<400> SEQUENCE: 38
taactccagt aattccttgg                                                 20

<210> SEQ ID NO 39
<211> LENGTH: 20
<212> TYPE: DNA
<213> ORGANISM: Artificial Sequence
<220> FEATURE:
<223> OTHER INFORMATION: gRNA

<400> SEQUENCE: 39
ggtccattgg tgaaagtttg                                                 20

<210> SEQ ID NO 40
<211> LENGTH: 20
<212> TYPE: DNA
<213> ORGANISM: Artificial Sequence
<220> FEATURE:
<223> OTHER INFORMATION: gRNA

<400> SEQUENCE: 40
attgcgatct ctttaaaggg                                                 20

<210> SEQ ID NO 41
<211> LENGTH: 51
<212> TYPE: DNA
<213> ORGANISM: Artificial Sequence
<220> FEATURE:
<223> OTHER INFORMATION: Primer
```

<400> SEQUENCE: 41
catggagtta ctgatgagtc cgtgaggacg aaacgagtaa gctcgtctaa c           51

<210> SEQ ID NO 42
<211> LENGTH: 60
<212> TYPE: DNA
<213> ORGANISM: Artificial Sequence
<220> FEATURE:
<223> OTHER INFORMATION: Primer

<400> SEQUENCE: 42
aaacgagtaa gctcgtctaa ctccagtaat tccttgggtt ttagagctag aaatagcaag    60

<210> SEQ ID NO 43
<211> LENGTH: 51
<212> TYPE: DNA
<213> ORGANISM: Artificial Sequence
<220> FEATURE:
<223> OTHER INFORMATION: Primer

<400> SEQUENCE: 43
catgtggacc ctgatgagtc cgtgaggacg aaacgagtaa gctcgtcggt c           51

<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44
aaacgagtaa gctcgtcggt ccattggtga agtttggtt ttagagctag aaatagcaag    60

<210> SEQ ID NO 45
<211> LENGTH: 51
<212> TYPE: DNA
<213> ORGANISM: Artificial Sequence
<220> FEATURE:
<223> OTHER INFORMATION: Primer

<400> SEQUENCE: 45
catgcgcaat ctgatgagtc cgtgaggacg aaacgagtaa gctcgtcatt g           51

<210> SEQ ID NO 46
<211> LENGTH: 60
<212> TYPE: DNA
<213> ORGANISM: Artificial Sequence
<220> FEATURE:
<223> OTHER INFORMATION: Primer

<400> SEQUENCE: 46
aaacgagtaa gctcgtcatt gcgatctctt taaaggggtt ttagagctag aaatagcaag    60

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47
gttttagagc tagaaatagc aagttaaaat aaggctagtc cgttatcaac ttgaaaagt    60

<210> SEQ ID NO 48
<211> LENGTH: 60

<212> TYPE: DNA
<213> ORGANISM: Artificial Sequence
<220> FEATURE:
<223> OTHER INFORMATION: Primer

<400> SEQUENCE: 48
cgccatgccg aagcatgttg cccagccggc gccagcgagg aggctgggac catgccggcc    60

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
aggctgggac catgccggcc aaaagcaccg actcggtgcc acttttcaa gttgataacg    60

<210> SEQ ID NO 50
<211> LENGTH: 51
<212> TYPE: DNA
<213> ORGANISM: Artificial Sequence
<220> FEATURE:
<223> OTHER INFORMATION: Primer

<400> SEQUENCE: 50
aagcagtcca agctgtccc attcgccatg ccgaagcatg ttgcccagcc g    51

<210> SEQ ID NO 51
<211> LENGTH: 230
<212> TYPE: DNA
<213> ORGANISM: Artificial Sequence
<220> FEATURE:
<223> OTHER INFORMATION: gRNA construct

<400> SEQUENCE: 51
catggagtta ctgatgagtc cgtgaggacg aaacgagtaa gctcgtctaa ctccagtaat    60
tccttgggtt ttagagctag aaatagcaag ttaaaataag gctagtccgt tatcaacttg   120
aaaaagtggc accgagtcgg tgcttttggc cggcatggtc ccagcctcct cgctggcgcc   180
ggctgggcaa catgcttcgg catggcgaat gggacagctt tggactgctt               230

<210> SEQ ID NO 52
<211> LENGTH: 230
<212> TYPE: DNA
<213> ORGANISM: Artificial Sequence
<220> FEATURE:
<223> OTHER INFORMATION: gRNA construct

<400> SEQUENCE: 52
catgtggacc ctgatgagtc cgtgaggacg aaacgagtaa gctcgtcggt ccattggtga    60 agtttggtt ttagagctag aaatagcaag ttaaaataag gctagtccgt tatcaacttg   120
aaaaagtggc accgagtcgg tgcttttggc cggcatggtc ccagcctcct cgctggcgcc   180
ggctgggcaa catgcttcgg catggcgaat gggacagctt tggactgctt               230

<210> SEQ ID NO 53
<211> LENGTH: 230
<212> TYPE: DNA
<213> ORGANISM: Artificial Sequence
<220> FEATURE:
<223> OTHER INFORMATION: gRNA construct

<400> SEQUENCE: 53

```
catgcgcaat ctgatgagtc cgtgaggacg aaacgagtaa gctcgtcatt gcgatctctt    60
taaaggggtt ttagagctag aaatagcaag ttaaaataag gctagtccgt tatcaacttg   120
aaaaagtggc accgagtcgg tgcttttggc cggcatggtc ccagcctcct cgctggcgcc   180
ggctgggcaa catgcttcgg catggcgaat gggacagctt tggactgctt              230

<210> SEQ ID NO 54
<211> LENGTH: 90
<212> TYPE: DNA
<213> ORGANISM: Artificial Sequence
<220> FEATURE:
<223> OTHER INFORMATION: dsDNA oligo

<400> SEQUENCE: 54
ctgttattaa tttcacaggt agttctggtc cattggtgaa agtatagttg cgccttgcag    60
agcacagagg ccgcagaatg tgctctagat                                     90

<210> SEQ ID NO 55
<211> LENGTH: 90
<212> TYPE: DNA
<213> ORGANISM: Artificial Sequence
<220> FEATURE:
<223> OTHER INFORMATION: dsDNA oligo

<400> SEQUENCE: 55
aagcgtatta caaatgaaac caagattcag attgcgatct cttaactagg ttggtcccct    60
agcgatagag cactcgatct tcccagaaaa                                     90

<210> SEQ ID NO 56
<211> LENGTH: 111
<212> TYPE: DNA
<213> ORGANISM: Artificial Sequence
<220> FEATURE:
<223> OTHER INFORMATION: dsDNA oligo

<400> SEQUENCE: 56
tcatgcacga aaagcaaaca aacttgtgtg cttcattgga tgttcgtacc taactaagta    60
attagttgaa gcattaggtc ccaaaatttg tttactaaaa acacatgtgg a            111

<210> SEQ ID NO 57
<211> LENGTH: 60
<212> TYPE: DNA
<213> ORGANISM: Artificial Sequence
<220> FEATURE:
<223> OTHER INFORMATION: Primer

<400> SEQUENCE: 57
gttttagagc tagaaatagc aagttaaaat aaggctagtc cgttatcaac ttgaaaaagt    60

<210> SEQ ID NO 58
<211> LENGTH: 60
<212> TYPE: DNA
<213> ORGANISM: Artificial Sequence
<220> FEATURE:
<223> OTHER INFORMATION: Primer

<400> SEQUENCE: 58
cgccatgccg aagcatgttg cccagccggc gccagcgagg aggctgggac catgccggcc    60

<210> SEQ ID NO 59
<211> LENGTH: 60
<212> TYPE: DNA
<213> ORGANISM: Artificial Sequence
```

```
<220> FEATURE:
<223> OTHER INFORMATION: Primer

<400> SEQUENCE: 59
aggctgggac catgccggcc aaaagcaccg actcggtgcc acttttttcaa gttgataacg    60

<210> SEQ ID NO 60
<211> LENGTH: 51
<212> TYPE: DNA
<213> ORGANISM: Artificial Sequence
<220> FEATURE:
<223> OTHER INFORMATION: Primer

<400> SEQUENCE: 60
aagcagtcca agctgtccc attcgccatg ccgaagcatg ttgcccagcc g              51

<210> SEQ ID NO 61
<211> LENGTH: 225
<212> TYPE: DNA
<213> ORGANISM: Artificial Sequence
<220> FEATURE:
<223> OTHER INFORMATION: MTH1

<400> SEQUENCE: 61
agtagctctc aatccacgac ttcttcgaga agagagaact ttgtgaatgc tcctccggag    60
tacactgata gagctagaga tgagattaaa aaaagattat tggcctcctc acctagcaga   120
aggtcacatc attcaagcag tatgcattca gcgagcagga gatcaagcgt ggctgaaagt   180
gggagtttac tttcggataa tgcctcgtct tatcaatcaa gtata                   225

<210> SEQ ID NO 62
<211> LENGTH: 20
<212> TYPE: DNA
<213> ORGANISM: Artificial Sequence
<220> FEATURE:
<223> OTHER INFORMATION: gRNA

<400> SEQUENCE: 62
ctctcttctc gaagaagtcg                                                20

<210> SEQ ID NO 63
<211> LENGTH: 20
<212> TYPE: DNA
<213> ORGANISM: Artificial Sequence
<220> FEATURE:
<223> OTHER INFORMATION: gRNA

<400> SEQUENCE: 63
agatcaagcg tggctgaaag                                                20

<210> SEQ ID NO 64
<211> LENGTH: 51
<212> TYPE: DNA
<213> ORGANISM: Artificial Sequence
<220> FEATURE:
<223> OTHER INFORMATION: Primer

<400> SEQUENCE: 64
catgagagag ctgatgagtc cgtgaggacg aaacgagtaa gctcgtcctc t              51

<210> SEQ ID NO 65
<211> LENGTH: 60
<212> TYPE: DNA
<213> ORGANISM: Artificial Sequence
<220> FEATURE:
```

<223> OTHER INFORMATION: Primer

<400> SEQUENCE: 65
aaacgagtaa gctcgtcctc tcttctcgaa gaagtcggtt ttagagctag aaatagcaag    60

<210> SEQ ID NO 66
<211> LENGTH: 51
<212> TYPE: DNA
<213> ORGANISM: Artificial Sequence
<220> FEATURE:
<223> OTHER INFORMATION: Primer

<400> SEQUENCE: 66
catgtgatct ctgatgagtc cgtgaggacg aaacgagtaa gctcgtcaga t             51

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
aaacgagtaa gctcgtcaga tcaagcgtgg ctgaaaggtt ttagagctag aaatagcaag    60

<210> SEQ ID NO 68
<211> LENGTH: 60
<212> TYPE: DNA
<213> ORGANISM: Artificial Sequence
<220> FEATURE:
<223> OTHER INFORMATION: Overlapping primer

<400> SEQUENCE: 68
gttttagagc tagaaatagc aagttaaaat aaggctagtc cgttatcaac ttgaaaaagt    60

<210> SEQ ID NO 69
<211> LENGTH: 60
<212> TYPE: DNA
<213> ORGANISM: Artificial Sequence
<220> FEATURE:
<223> OTHER INFORMATION: Overlapping primer

<400> SEQUENCE: 69
cgccatgccg aagcatgttg cccagccggc gccagcgagg aggctgggac catgccggcc    60

<210> SEQ ID NO 70
<211> LENGTH: 60
<212> TYPE: DNA
<213> ORGANISM: Artificial Sequence
<220> FEATURE:
<223> OTHER INFORMATION: Overlapping primer

<400> SEQUENCE: 70
aggctgggac catgccggcc aaaagcaccg actcggtgcc acttttttcaa gttgataacg    60

<210> SEQ ID NO 71
<211> LENGTH: 51
<212> TYPE: DNA
<213> ORGANISM: Artificial Sequence
<220> FEATURE:
<223> OTHER INFORMATION: Overlapping primer

<400> SEQUENCE: 71
aagcagtcca agctgtccc attcgccatg ccgaagcatg ttgcccagcc g              51

```
<210> SEQ ID NO 72
<211> LENGTH: 230
<212> TYPE: DNA
<213> ORGANISM: Artificial Sequence
<220> FEATURE:
<223> OTHER INFORMATION: gRNA construct

<400> SEQUENCE: 72
catgagagag ctgatgagtc cgtgaggacg aaacgagtaa gctcgtcctc tcttctcgaa      60
gaagtcggtt ttagagctag aaatagcaag ttaaaataag gctagtccgt tatcaacttg     120
aaaaagtggc accgagtcgg tgcttttggc cggcatggtc ccagcctcct cgctggcgcc     180
ggctgggcaa catgcttcgg catggcgaat gggacagctt tggactgctt                230

<210> SEQ ID NO 73
<211> LENGTH: 230
<212> TYPE: DNA
<213> ORGANISM: Artificial Sequence
<220> FEATURE:
<223> OTHER INFORMATION: gRNA construct

<400> SEQUENCE: 73
catgtgatct ctgatgagtc cgtgaggacg aaacgagtaa gctcgtcaga tcaagcgtgg      60
ctgaaaggtt ttagagctag aaatagcaag ttaaaataag gctagtccgt tatcaacttg     120
aaaaagtggc accgagtcgg tgcttttggc cggcatggtc ccagcctcct cgctggcgcc     180
ggctgggcaa catgcttcgg catggcgaat gggacagctt tggactgctt                230

<210> SEQ ID NO 74
<211> LENGTH: 504
<212> TYPE: DNA
<213> ORGANISM: Artificial Sequence
<220> FEATURE:
<223> OTHER INFORMATION: dsDNA oligo

<400> SEQUENCE: 74
ggaatatctg ccattctacc ccttattcaa gtgcctttt tttttttttt catcccacat       60
tttattgctg cctcaatctc cattaagaaa aaaaatttat ataaccaaat gacattttc      120 ctttcttctc aaactttgta atgcgcctgt aactgcttct tttttatta aaaaacagca      180 tggagttttt taataactta aggaaacata caaaaagatt tgttcatttc actccaagta     240 tttttttaaag tatattgaaa gttctcaata gcgaaaccac aagcagcaat acaaagagaa    300
ttttattcga acgcatagag tacacacact caaaggaatg tttgtttcac caccaccagc    360
aacttcgaaa aaccaagttt tacaacgacg tccattagaa tcgactaaca gtaatcatgg    420
gtttgcaagc tccctacagg ccattccgga aaacacgatg agtggcagtg ataatgcttc    480
ttttcaaagt ttgccactat caat                                            504

<210> SEQ ID NO 75
<211> LENGTH: 498
<212> TYPE: DNA
<213> ORGANISM: Artificial Sequence
<220> FEATURE:
<223> OTHER INFORMATION: dsDNA oligo

<400> SEQUENCE: 75
gttttctgcc ccctctactg tgcacacgca actaactaat gactcttcgt tctccgaatt      60
tcctaaccac aagttaatca cgagagtgag cctggatgaa gcattaccca aaacgtttta    120
tgacatgtat tcgccagata ttctattagc agacccatcc aacattctct gtaacgggcg    180
```

```
tcccaagttt accaagagag agttattgga ttgggattta aacgatataa gatcgttatt    240
gatagtcgag aagttaaggc ccgaatgggg taatcaacta ccggaagtaa taacggtggg    300
tgataatatg ccccagttta ggttacaatt attaccacta tattctagcg atgagaccat    360
aatcgcaacg ttagtccatt cggatctgta catggaggct aacttagatt atgaattcaa    420
actaaccagc gccaaatata cagtagcgac cgctagaaaa agacatgagc atataactgg    480
tagaaatgaa gccgtcat                                                  498

<210> SEQ ID NO 76
<211> LENGTH: 20
<212> TYPE: DNA
<213> ORGANISM: Artificial Sequence
<220> FEATURE:
<223> OTHER INFORMATION: primer fw

<400> SEQUENCE: 76
ggaatatctg ccattctacc                                                 20

<210> SEQ ID NO 77
<211> LENGTH: 31
<212> TYPE: DNA
<213> ORGANISM: Artificial Sequence
<220> FEATURE:
<223> OTHER INFORMATION: overlapping primer rev

<400> SEQUENCE: 77 gaggggggcag aaaacattga tagtggcaaa c                                   31

<210> SEQ ID NO 78
<211> LENGTH: 31
<212> TYPE: DNA
<213> ORGANISM: Artificial Sequence
<220> FEATURE:
<223> OTHER INFORMATION: Overlapping primer rev

<400> SEQUENCE: 78
gtttgccact atcaatgttt tctgccccct c                                    31

<210> SEQ ID NO 79
<211> LENGTH: 20
<212> TYPE: DNA
<213> ORGANISM: Artificial Sequence
<220> FEATURE:
<223> OTHER INFORMATION: primer rev

<400> SEQUENCE: 79
atgacggctt catttctacc                                                 20

<210> SEQ ID NO 80
<211> LENGTH: 20
<212> TYPE: DNA
<213> ORGANISM: Artificial Sequence
<220> FEATURE:
<223> OTHER INFORMATION: primer fw

<400> SEQUENCE: 80
tacgagtcca tttctccagt                                                 20

<210> SEQ ID NO 81
<211> LENGTH: 20
<212> TYPE: DNA
<213> ORGANISM: Artificial Sequence
<220> FEATURE:
<223> OTHER INFORMATION: Primer rev
```

```
<400> SEQUENCE: 81
attgtgcctc tactgctata                                               20

<210> SEQ ID NO 82
<211> LENGTH: 30
<212> TYPE: DNA
<213> ORGANISM: Artificial Sequence
<220> FEATURE:
<223> OTHER INFORMATION: Amplification primer fw

<400> SEQUENCE: 82
agaagacgct agcgatgaaa ccataatcgc                                    30

<210> SEQ ID NO 83
<211> LENGTH: 38
<212> TYPE: DNA
<213> ORGANISM: Artificial Sequence
<220> FEATURE:
<223> OTHER INFORMATION: Amplification primer rev

<400> SEQUENCE: 83
ggttacaatt attaccacta tattctagcg cgtcttct                           38
```

US 10,947,571 B2

METHOD FOR PRODUCING LACTIC ACID IN RECOMBINANT YEAST CELL CULTURE

CROSS-REFERENCE TO RELATED APPLICATIONS

This application is the U.S. national stage of International Patent Application No. PCT/EP2017/059046, filed on Apr. 14, 2017 and entitled METHOD FOR PRODUCING LACTIC ACID, which claims the benefit of priority under 35 U.S.C. § 119 from European Patent Application No. 16165772.1, filed Apr. 18, 2016. The disclosures of the foregoing applications are incorporated herein by reference in their entirety.

SEQUENCE LISTING

The entire content of a Sequence Listing titled "Sequence_Listing.txt," created on Jul. 9, 2018 and having a size of 22 kilobytes, which has been submitted in electronic form in connection with the present application, is hereby incorporated by reference herein in its entirety.

FIELD OF THE INVENTION

The present invention provides a method for producing lactic acid in a recombinant yeast cell culture using glucose as carbon source comprising a first, seed fermentation stage to produce biomass wherein the yeast is cultivated in a culture medium at a pH of 5 to 7, followed by a second, a production fermentation stage with biomass from the seed fermentation to produce lactic acid, wherein the yeast is cultivated in a culture medium at low pH using a yeast strain that is engineered to have lactate dehydrogenase (LDH) activity or to have lactate dehydrogenase (LDH) activity and decreased or knocked-out pyruvate decarboxylase (PDC) activity.

BACKGROUND OF THE INVENTION

Lactic acid is ranked by the US Department of Energy among the top 30 chemical building block candidates from sugars showing significant market growth. The global lactic acid market in 2013 was estimated at 714,200 t and is expected to expand to 1,960,100 t by 2020, with a growth rate between 2014 and 2020 of 15.5% compound annual growth rate (CAGR).

Lactic acid has long been used in the food industry as a preservative and as acidulant. The price of lactic acid is currently around $1.30-$1.60 per kg. It is also used as a solvent, particularly in esterified form, and a raw material in the pharmaceutical, cosmetic and chemical industries as well as for the production of lactate esters. Lactic acid is increasingly used as a starting material in the production of polylactic acid (PLA), a biodegradable plastic made from renewable resources.

The major forces for market growth of lactic acid are the use in the development of biodegradable polymers and lactate solvents. Personal care is also expected to be a fast growing segment, since lactic acid is used in products for skin lightening, anti-acne, anti-wrinkle and anti-aging.

Polylactic acid (PLA) accounted for 11.4% (approx. 185 kt) of the global bioplastics market in 2013. PLA is predicted to have an annual market growth of 18.8% CAGR, resulting in a market volume of 438 kt in 2018. The quality of PLA and its range of technical applications have developed rapidly over the last few years. Today PLA is used in three major application areas:

1. Fibre: in clothing, carpets, furnishings, nonwovens and other industrial applications
2. Film and packaging: fresh food packaging and other applications such as food service ware
3. Engineering applications: in electronics, consumer goods, the automotive industry Biodegradable plastic from renewable resources (bioplastics) has a wide range of advantages compared with petrochemical plastics. Overcoming the price barrier for PLA compared to petrochemical plastics will make these advantages available to a wide range of applications.

The benefits of bioplastics during its lifecycle are:
Derived from renewable feedstock
No depletion of valuable crude oil resources
Low carbon footprint—which is believed to be at least 30% lower than conventional oil-based plastics
Biodegradable
Avoids problems associated with landfill and littering.

Producing the starting material for PLA—lactic acid—at half the current price will significantly influence the cost of PLA products. This offers the chance to boost the market position of PLA compared to more expensive petrochemical plastic products.

Lactic acid is traditionally produced using lactic acid bacteria. For the food industry in particular, these are the production organisms of choice, because they produce the acid naturally. Examples of traditional foods containing lactic acid are sauerkraut and yoghurt. Isolated lactic acid, derived from glucose by lactic acid-fermenting bacteria, is also used in the modern food processing industry. The main use of lactic acid in the chemical industry is the manufacture of the plastic polylactate (PLA).

The demand placed on lactic acid as raw material for the manufacture of plastics, is, however, much higher than for use in food. The lactic acid must be of high purity, particularly enantiomerically pure (i.e. it must be pure D- or L-lactic acid) and it must be very inexpensive because PLA is currently in competition with cheap conventional petrochemical plastics. A crucial factor for the price of lactic acid is its purification after fermentation. Purification is difficult and expensive, in part because lactic acid bacteria cannot tolerate low pH values during the fermentation process, in part because they are dependent on organic nitrogen sources. Furthermore, lactic acid bacteria usually accumulate both enantiomers of the acid (Sauer et al., 2008, Trends Biotechnol. 26, 100-108 and Sauer M. et al., 2010, Biotechnol. Gen. Engineering, 27, 229-256). The pH value in particular poses a problem because the purification of the free lactic acid can be effected only from solutions with a low pH. This means that during fermentation the pH must be kept high by adding base. For purification of the lactic acid, the fermentation broth must be acidified and the resulting salt (Gypsum) must be disposed of or recycled, which is a technically complex procedure.

A solution to these problems is the production of lactic acid by recombinant yeasts. These are more acid tolerant than lactic acid bacteria, can grow and produce on mineral media, and accumulate only the desired lactic acid enantiomer. NatureWorks LLC (Cargill) is one of the few commercial manufacturers of PLA. The lactic acid, which serves as the basis for the manufacture of PLA is produced by a yeast-based process (about 140,000 t per year). NatureWorks' process is based on a recombinant Crabtree-negative yeast (Miller et al. 2011, Industrial production of lactic acid, Elsevier, 179-188). The fermentation process yields 100-130 g/l lactic acid in 40-45 hours, at a final pH value of 3. This lactic acid is not, however, available on the open market, but is processed on the same site into PLA.

The fermentation of glucose to ethanol by baker's yeast is one of the most efficient bioprocesses in existence. It is believed that productivity is limited only by the glucose uptake rate from the medium into the cell. Pyruvic acid (pyruvate) is the key glucose-derived metabolite used in the production of ethanol. If the metabolic pathway for ethanol is eliminated by deleting the pyruvate decarboxylase (PDC) activity and simultaneously inserting a lactate dehydrogenase (LDH), which converts pyruvic acid into lactic acid, a yeast strain is created which produces lactic acid instead of ethanol. Such strains have already been developed in various preliminary projects (Branduardi et al. 2006, Microbial Cell Factories, 5:4, 1-12).

WO2004/099425 refers to such a method for producing lactic acid without producing a significant amount of ethanol using haploid Crabtree positive yeasts grown in an aerobic environment with glucose that lack pyruvate decarboxylase activity and comprise an exogenous lactate dehydrogenase gene.

WO2009/144013 describes a method for producing lactic acid using yeast overexpressing a hexose transporter gene which leads to an increase in the productivity of the organic acid.

However, although several attempts have been made to improve lactic acid producing yeasts, there is still an unmet demand to provide an improved process for reproducing high amounts of pure isomeric lactic acid without the need of expensive purification processes.

SUMMARY OF THE INVENTION

Said demand is solved by the embodiments of the invention.

The present invention provides genetically modified yeast strains to produce optically pure isomers of lactic acid, L(+)-lactic acid or D(−)-lactic acid, dependent on the genetically modified yeast strains used. In aligning the specific metabolic needs of these yeast strains with the inventive approaches in bioprocess engineering, the present process can significantly reduce the production costs of lactic acid. The purity of the fermentation broth in the inventive process is a great advantage compared with conventional processes using lactic acid bacteria as these require organic nitrogen sources and a high pH value, both of which add to the cost of purification. Compared to established processes based on yeast systems, the inventive process has the particular advantage of greater productivity, enabling higher throughput due to significantly reduced fermentation time and thus a lower price for the product. The present process is characterized by particularly high productivity at low pH values on mineral media.

A major problem of fermentation at low pH value is the limited viability of the strains, especially at high lactic acid concentrations. This significantly limits overall productivity. The innovative aspect of the present process involves keeping the time in which the cells are exposed to stress conditions during the efficient production of lactic acid down to a minimum. This is achieved by the two-step process, which separates the cell growth phase from the lactic acid production phase both temporally and optionally also spatially.

The first stage of the fermentation process involves a rapid increase in the yeast biomass and in the second stage glucose is converted into lactic acid. This avoids the inhibitory effect of lactic acid on growth during yeast proliferation, and once high cell density has been reached, it achieves a maximum lactic acid yield with high productivity.

The subsequent purification of lactic acid can be performed by standard methods. The process provides a fermentation broth which can be purified by conventional techniques. Moreover, the fermentation process at low pH value makes the purification process cheaper, since it is no longer necessary to acidify the fermentation broth prior to purification, which in turn makes the removal of large quantities of salts unnecessary.

The present invention provides a method for producing lactic acid in a recombinant yeast cell culture using glucose as carbon source comprising the sequential stages of a seed fermentation stage to produce biomass wherein the yeast is cultivated in a culture medium at a pH of 5 to 7, followed by a production fermentation stage with biomass from the seed fermentation to produce lactic acid, wherein the yeast is cultivated in a culture medium at a pH of <5, and wherein said yeast is modified to have lactate dehydrogenase (LDH) activity or LDH activity and decreased or knocked-out pyruvate decarboxylase (PDC) activity.

Within the embodiment is also a method for producing lactic acid in a recombinant yeast cell culture containing glucose as carbon source comprising the steps of a) cultivating yeast cells at a pH of 5 to 7 in a seed fermentation to produce biomass b) harvesting and optionally washing the cells of step a), c) inoculating a production fermentation with said cells at an $OD^{600}$ of at least 3.0 d) incubating said cells under conditions to produce lactic acid at a pH of <5, specifically until a final pH of less than 2.5 is reached, and e) purifying lactic acid from the cell culture or cell culture supernatant, wherein said yeast is a diploid, or optionally a polyploid or aneuploid yeast which has recombinant lactate dehydrogenase (LDH) activity and optionally decreased pyruvate decarboxylase (PDC) activity.

Within the embodiment is also a method for producing lactic acid in a recombinant yeast cell culture containing glucose as carbon source comprising the steps of a) cultivating yeast cells at a constant pH of 5 to 7 in a seed fermentation under conditions to reach an OD of at least 10, b) cultivating said cells until a final pH of less than 2.5 is reached to produce lactic acid, and c) purifying lactic acid from the cell culture or cell culture supernatant, wherein said yeast is a diploid yeast, or optionally a polyploid or aneuploid yeast which has lactate dehydrogenase (LDH) activity and optionally decreased pyruvate decarboxylase (PDC) activity.

Said recombinant yeast used for the inventive process is therefore metabolically engineered for efficient lactic acid production.

According to an embodiment of the invention, the yeast strain is capable of producing about 80 g/L LA/100 g/L glucose, specifically about 100 g/L LA per 120 g/L glucose, more specifically about 120 g/L per 150 g/L glucose or producing even greater amounts. Specifically, the final pH of such production medium is <3.

According to an embodiment of the invention, lactic acid is purified from the fermentation stage by common industrial processes and specifically has a purity of at least 90%, specifically of at least 95%, specifically of at least 99%, more specifically it is free from any impurities.

In a specific embodiment, the production fermentation stage is at a pH of ≤4.5, specifically ≤4, specifically ≤3.5, more specifically the production fermentation stage has a final pH of 3, more specifically the production fermentation stage has a final pH of ≤2.9, ≤2.8, ≤2.7, ≤2.6, ≤2.5, ≤2.4, ≤2.3, ≤2.2, ≤2.15 or less.

In some embodiments, the seed fermentation stage is performed under fed-batch conditions.

In some embodiments, the production fermentation stage is performed under batch process conditions.

According to the invention, seed fermentation and production fermentation can be performed in the same container.

According to a specific embodiment of the invention, the seed fermentation stage and the production fermentation stage are in separate fermenters.

According to a certain embodiment of the invention, the initial concentration of sugar in the production fermentation stage is at least 10% (w/w), specifically 12% (w/w) or more, more specifically 15% or more, and more preferred 20% or more.

According to a certain embodiment of the invention, the initial concentration of glucose in the production fermentation stage is at least 10% (w/w), specifically 12% (w/w) or more, more specifically 15% or more, and more preferred 20% or more.

In another embodiment, the process is based on sucrose. The initial concentration of sucrose in the production fermentation stage is at least 10% (w/w), specifically 12% (w/w) or more, more specifically 15% or more, and more preferred 20% or more.

According to an embodiment, lactic acid is produced in free form, specifically it is produced in optically pure isomeric form, specifically either D(-) or L(+)-lactic acid. The inventive method can be performed by recombinant yeast comprising a heterologous lactate dehydrogenase (LDH) gene, either stably integrated into the genome or on a plasmid or vector or expression cassette applicable for functional and stable gene expression. Said yeast is capable of producing lactic acid at a pH of less than 3.5, specifically at a pH of less than 3, more specifically at a pH of less than 2.8, more specifically at a pH of less than 2.5, more specifically a pH of less than 2.2.

Introducing the exogenous LDH gene can be performed by methods known by the skilled person, for example transformation, specifically by electroporation, microprojectile bombardment, LiAc/ss/DNA/PEG method, use of the CRISPR-cas9 system etc.

According to a further embodiment, said recombinant yeast has decreased or knocked out expression of one or more of the genes encoding PDC1, PDC5 and/or PDC6.

According to a specific embodiment, the recombinant yeast has decreased or knocked out expression of one or more of the genes encoding PDC1, PDC5 and/or PDC6 due to substitution and/or deletion of one or more of promotors of PDC1, PDC5 and/or PDC6 genes.

In an alternative embodiment the recombinant yeast has the genes encoding PDC1, PDC5 and/or PDC6 conditionally expressed, specifically due to the control of heterologous promoters, specifically due to glucose repressible promoters, more specifically due to the control of HXT2 or HXT4 gene promoters.

In an alternative embodiment, at least one of the genes encoding PDC1, PDC5 and/or PDC6 is deleted in the recombinant yeast.

In a further specific embodiment of the invention, the yeast has decreased or knocked-out expression of one or more genes encoding proteins interacting with glucose sensors controlling glucose-regulated gene expression, specifically expression of Std1 or Mth1 proteins.

Specifically, the MTH1 gene is partially or completely deleted.

In a further embodiment, the yeast is modified to overexpress at least one hexose transporter gene, specifically the yeast is modified to overexpress at least one of hexose transporter genes selected from the group of HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3 and RGT2.

Further provided by the embodiments of the present invention is a recombinant yeast having lactate dehydrogenase (LDH) activity and optionally also decreased or knocked out pyruvate decarboxylase (PDC) activity as described herein.

According to a further embodiment, the recombinant yeast may also have decreased or knocked-out pyruvate dehydrogenase activity.

The present invention further provides a recombinant yeast strain, comprising
  i) functionally deleted PDC1, PDC5 and PDC6 genes,
  ii) functionally deleted MTH1 gene,
  iii) overexpressed HXT1 gene, and
  iv) at least one heterologous LDH gene.

The recombinant yeast strain used according to the invention may belong to the genus selected from *Saccharomyces, Candida, Schizosaccharomyces, Torulaspora, Kluyveromyces, Zygosaccharomyces, Sugiyamaella, Komagataella* and *Dekkera*.

In certain embodiments, the yeast strain is selected from *Kluyveromyces thermotolerans, Kluyveromyces lactis, Torulaspora delbrueckii, Zygosaccharomyces bailii, Schizosaccharomyces pombe, Sugiyamaella lignohabitans, Komagataella pastoris, Komagataella phaffii* and *Candida glabrata*.

The most preferred belongs to *Saccharomyces*, specifically it is *Saccharomyces cerevisiae, Saccharomyces bayanus, Saccharomyces boulardii* or *Saccharomyces paradoxus*.

The recombinant yeast may be haploid or diploid, preferably diploid.

As an alternative, the yeast cells can also be aneuploid or polyploid cells.

According to a preferred embodiment, the recombinant yeast cells are stress resistant.

Preferably, the yeast cells are diploid yeast cells, since diploid yeasts are often more stress resistant and robust. The yeast shall also preferably be isolated from stressful environments, such as high sugar environments, like fruit juice or sugar cane juice or isolated using adaptive laboratory evolution (ALE) using selective pressure for evolutionary engineering, as exemplarily described in Cakar Z. P. et al, (FEMS Yeast Res. 12, 2012, 171-182). Evolutionary engineering involves the more systematic approach of repeated batch cultivations performed in the presence of a selective pressure, or alternatively, prolonged chemostat cultivations performed under selective conditions. Those cultivations can be performed with a wild-type or, to increase genetic diversity, a chemically or physically mutagenized strain. Spontaneous or induced mutagenesis of the initial monoclonal population results in the formation of fitter variants in the initial monoclonal population as a consequence of the selection pressure applied throughout the cultivations. These fitter variants can survive and grow better than the original cells under the selection conditions. Thus, in chemostat or serial batch cultures, the ratio of the number of fitter cells to the total number of cells in the culture will periodically increase, and the fitter cells will dominate the culture (Cakar, 2012, Sauer U (2001), Adv Biochem Eng Biotechnol 73: 130-166.).

In a specific embodiment, yeast cells may be pre-cultivated or cultivated for at least 50, 60, 70, 80 90, 100 or more generations under stress conditions before the cells are transferred to seed fermentation and production fermentation. Said stress conditions may be, but are not limited high sugar concentration, specifically sucrose or glucose concentration, sugar limitation, nitrogen depletion, sulfite, low pH, hyper osmotic challenge caused by high solute concentrations, hypo osmolarity, oxidative stress due to aerobiosis or anaerobiosis, hydrostatic pressure, increased acetaldehyde or ethanol concentration, internal acidification, starvation., thermal stress, i.e. cultivation outside the optimum temperature of about 25-30° C.

Specifically, stress conditioning of the yeast cells is performed under increased glucose concentrations. Specifically the glucose concentration may be about 110 g/l, 120 g/l, 130 g/l, 150 g/l, 160 g/l or more.

According to an embodiment, said recombinant stress resistant diploid yeast cells are genetically modified as described herein. Specifically said cells are glucose tolerant with a higher growth rate than the parent strain, when both grown on the same medium.

Saccharomyces cerevisiae is available from a variety of sources including, but not limited to, American Type Culture Collection (Rockville, Md.), Centraalbureau voor Schimmelcultures (CBS) Fungal Biodiversity Centre, LeSaffre, Gert Strand Aft Ferm Solutions, North American Bioproducts, Martrex, and Lallemand. S. cerevisiae include, but are not limited to, BY4741, CEN. PK 113-7D, Ethanol Red® yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, GRF18U, BG-1, PE-2, CAT-1, CBS1585, CBS2910, CBS7833, CBS7834, 7835, CBS7836, CBS7837, CBS7838, 7839, CBS7840, CBS7959, CBS7960, and CBS7961, CBS7962, CBS9562, CBS9563, CBS9564, CBS9565, CEN. PK113-7D, CLIB215, CLIB324, CLIB382, EC1118, EC9-8, FL100, Fleischmanns baking yeast, FostersB, FostersO, FY, G600, GSY1135, 114, IL-01, IR-2, JAY291, JWY6147, KRY8, LAN211, Lindquist 5672, M1-2, M13, M14, M2-8, M22, M32, M34, M3707, M3836, M3837, M3838, M3839, M5, M52bB, M52cW, M8, MMY112, MUCL28177, N85, NAM34-4C, NC-02, NRRL Y-12632, NY1308, P283, P301, PE-2, PW5, E008, R103, Red Star baking yeast, RM11-1A, S228, S288c, SGU57, Sigma1278b, SK1, T7, T73, UCS, UFMG A 905, Vin13, VL3, W303, WE372, Y10, Y12, Y2209, Y389, Y9, YB210, YJM1004, YJMI1005, YJMI1006, YJMI1978, YJMI1083, YJMI1094, YJM11095, YJMI1096, YJMI1097, YJMI1098, YJMI1099, YJMI1100, YJMI1101, YJMI1102, YJMI1103, YJMI1104-YJMI1122, YJMI1124, YJMI1125, YJMI1129, YJMI1133, YJMI1135, YJMI1138, YJMI1139, YJMI1140, YJMI1141, YJMI1142, YJMI1143, YJMI1144, YJMI1145, YJMI1146, YJMI1178, YJMI1190, YJMI1199, YJMI1202, YJMI1208, YJMI1242, YJMI1244, YJMI1248, YJM11250, YJMI1252, YJMI1259, YJMI1273, YJMI1289, YJMI1292, YJMI1304, YJMI1307, YJMI1311, YJMI1326, YJMI1336, YJMI1338, YJMI1341, YJMI1342, YJMI1355, YJMI1356, YJMI1381, YJMI1383, YJMI1385, YJMI1386, YJMI1387, YJMI1388, YJMI1389, YJMI1399, YJMI1400, YJMI1401, YJMI1402, YJMI1415, YJMI1417, YJMI1418, YJMI1419, YJMI1433, YJMI1434, YJMI1439, YJMI1443, YJMI1447, YJMI145, YJMI1450, YJMI1460, YJMI1463, YJMI1477, YJMI1478, YJMI1479, YJMI1526, YJMI1527, YJMI1549, YJMI1573, YJMI1574, YJMI1592, YJMI1615, YJMI189, YJMI193, YJMI195, YJM1223, YJM1244, YJM1248, YJM1269, YJM1270, YJM1271, YJM1280, YJM1308, YJM1320, YJM1326, YJM1332, YJM1339, YJM1421, YJM1428, YJM1432, YJM1434, YJM1435, YJM1436, YJM1437, YJM1439, YJM1440, YJM1450, YJM1451, YJM1453, YJM1454, YJM1455, YJM1456, YJM1464, YJM1466, YJM1467, YJM1470, YJM1521, YJM1525, YJM1541, YJM1554, YJM1555, YJM1560, YJM1561, YJM1627, YJM1634, YJM1653, YJM1669, YJM1670, YJM1671, YJM1672, YJM1674, YJM1676, YJM1677, YJM1678, YJM1681, YJM1682, YJM1683, YJM1689, YJM1693, YJM1789, YJM1810, YJM1811, YJM1813, YJM1815, YJM1816, YJM1936, YJM1945, YJM1946, YJM1947, YJM1948, YJM1949, YJM1950, YJM1951, YJM1952, YJM1953, YJM1954, YJM1955, YJM1956, YJM1957, YJM1958, YJM1959, YJMI960, YJMI961, YJM1962, YJM1963, YJM1964, YJM1965, YJM1966, YJM1967, YJM1969, YJM1972, YJM1975, YJM1978, YJM1981, YJM1984, YJM1987, YJMI990, YJM1993, YJM1996, YJSH1, YPH499N, YPS1009, YPS163, ZTW1.

In a specific embodiment, the Saccharomyces cerevisiae is the strain CBS7962, CBS7959, CBS7960, or CBS7961.

In a specific embodiment, the yeast strain can be auxotrophic for uracil, leucine, tryptophan and/or histidine. Specifically, the strain is auxotroph for ura, trp and his by inactivating the genes encoding therefor.

The embodiments of the invention also provide a sequential two step fermentation system for producing lactic acid with a sugar, such as glucose or sucrose as carbon source using a recombinant yeast strain, consisting of a) a seed fermentation stage to produce biomass, wherein the yeast is cultivated in a culture medium at a pH of 5 to 7, followed by b) a production fermentation stage to produce lactic acid, wherein the yeast is cultivated in a cell culture medium at a pH of less than 3.5, specifically until a final pH of about 3, more specifically until a final pH of about 2.8, about 2.7, about 2.6, about 2.5, about 2.4, about 2.3, about 2.2, more specifically until a final pH of about 2.1., wherein the yeast encodes heterologous lactate dehydrogenase (LDH) activity and has decreased or diminished PDC activity.

Alternatively, a two stage fermentation system for producing lactic acid with a sugar, such as glucose or sucrose as carbon source using a recombinant yeast strain is provided, consisting of a) a seed fermentation stage in a first fermenter to produce biomass, wherein the yeast is cultivated in a culture medium at a pH of 5 to 7, followed by b) a production fermentation stage in a second fermenter inoculated from the seed fermentation to produce lactic acid, wherein the yeast is cultivated in a cell culture medium at a pH of less than 3.5, specifically until a pH of about 3, more specifically until a pH of about 2.8, about 2.7, about 2.6, about 2.5, about 2.4, about 2.3, about 2.2, more specifically until a pH of about 2.1., wherein the yeast is modified to have lactate dehydrogenase (LDH) and/or decreased pyruvate decarboxylase (PDC) activity.

In yet a further embodiment a combination of two fermenter systems for producing lactic acid with glucose as carbon source using a recombinant yeast strain, consisting of a) a seed fermenter to produce biomass, wherein the yeast is cultivated in a culture medium at a pH of 5 to 7, followed by b) a production fermenter inoculated from the seed fermentation to produce lactic acid, wherein the yeast is cultivated in a cell culture medium at a pH of less than 3.5, specifically at a final pH of about 3 or lower, more specifically until a pH of about 2.8, about 2.7, about 2.6, about 2.5, about 2.4, about 2.3, about 2.2, more specifically until a pH of about 2.1., wherein the yeast has lactate dehydrogenase (LDH) activity and decreased or no pyruvate decarboxylase (PDC) activity.

FIGURES

FIG. 1: Differences in the manufacturing process using lactic acid bacteria vs. genetically modified yeasts in a two-stage fermentation process (process of the invention).

Figure 2:
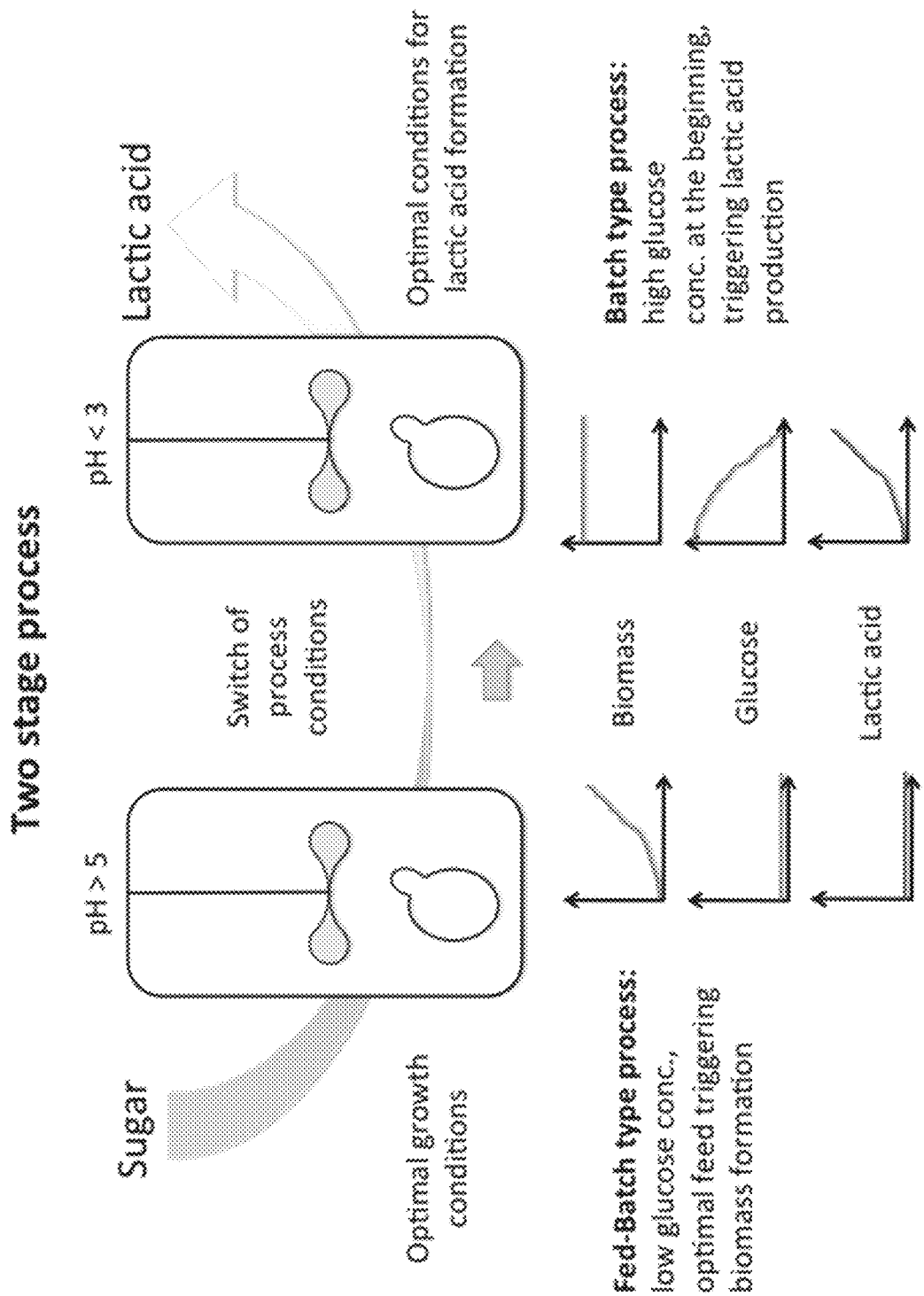

FIG. 2: Two stage fermentation process divided into biomass growth and lactic acid formation.

DETAILED DESCRIPTION OF THE INVENTION

The present invention provides a novel method for producing lactic acid using recombinant yeast.

Lactic acid (2-hydroxypropionic acid) is an organic compound with the formula $CH_3CH(OH)CO_2H$. With a hydroxyl group adjacent to the carboxyl group, lactic acid is classified as an alpha hydroxy acid (AHA). In the form of its conjugate base called lactate, it plays a role in several biochemical processes.

In solution, it can ionize a proton from the carboxyl group, producing the lactate ion $CH_3CH(OH)CO_2^-$. Compared to acetic acid, its $pK_a$ is 1 unit less, meaning lactic acid deprotonates ten times more easily than acetic acid does. This higher acidity is the consequence of the intramolecular hydrogen bonding between the α-hydroxyl and the carboxylate group.

Lactic acid is chiral, consisting of two optical isomers. Lactic acid is the simplest hydroxyl acid that is optically active. L(+)-lactic acid can be produced directly without D(−)-lactic acid through fermentation (e.g., known chemical syntheses produce racemic mixtures of both isomers). Likewise D(−)-lactic acid can be produced by fermentation without L(+)-lactic acid. One is known as L(+)-lactic acid or (S)-lactic acid and the other, its mirror image, is D(−)-lactic acid or (R)-lactic acid. A mixture of the two in equal amounts is called DL-lactic acid.

Lactic acid is hygroscopic. DL-lactic acid is miscible with water and with ethanol above its melting point which is around 17 or 18° C. D-lactic acid and L-lactic acid have a higher melting point.

The term "culture medium" refers to a solid or liquid medium comprising sufficient nutrients, including a sugar such as, but not limited to, glucose or sucrose as carbon source, on which the recombinant yeast can grow. In chemostat, fed-batch, or batch cultures the medium is a liquid.

The terms "seed fermentation stage" and "inoculum development stage" as used herein refer to the provision of cultivation conditions wherein recombinant yeast is grown to high densities, which can be used for inoculation of the production fermentation stage. Seed fermentation is thus performed under conditions which are optimal for the growth of the recombinant yeast (biomass growth phase).

Seed fermentation is performed at a pH of about 5.0 to 7.0, specifically, the pH is about 5.0.

Optionally, the first stage is glucose or sucrose limited (e.g., less than about 10 g/l, preferably less than 5 g/L, more preferably less than 2 g/L). Glucose or sucrose is used herein as main carbon source for seed fermentation, specifically the glucose content of the seed fermentation medium at inoculation is between 10 and 25 g/l, specifically between 15 and 25 g/l, more specifically at about 20 g/l.

Low glucose concentration in this context means less than 10 g/L glucose for cultivation, specifically less than 5 g/L, specifically less than 2 g/L. As an alternative, other carbon sources may be applicable, for example but not limited lignocellulose derived sugars, lignocellulose hydrolysates, xylose, arabinose, mannose, galactose or fructose or any mixtures thereof.

Further, a nitrogen source is provided.

Seed fermentation can specifically be performed as a fed-batch process or batch process, the fed-batch being preferred.

Under fed batch conditions, the batch culture proceeds until complete or almost complete consumption of glucose and ethanol before a fresh medium is fed into the culture. The feed-medium preferably contains high concentrations of glucose or sucrose, specifically between 20 g/l and about 500 g/L The yeast is cultivated at a flow rate necessary to maintain the specific growth rate at the critical value which is strain specific and can be determined using prior to chemostat cultivations. If the growth rate exceeds a critical value, the respiratory capacity of the yeast will be exceeded and fermentation of the substrate will occur, even in the presence of oxygen. Maintaining the specific growth rate at the critical value ensures high biomass yield per substrate consumed without forming by-products such as ethanol, lactate, glycerol and acetate.

High sugar concentration in this context means 10 g/L sugar, specifically 20 g/L sugar or more for cultivation.

High glucose concentration in this context means 10 g/L glucose, specifically 20 g/L glucose or more for cultivation.

High sucrose concentration in this context means 10 g/L sucrose, specifically 20 g/L sucrose or more for cultivation.

Preferably, the seed fermentation stage is aerobic.

In certain embodiments, the controlled variable for increasing biomass can be selected from the group consisting of respiratory quotient (RQ), specific oxygen uptake rate, specific carbon dioxide evolution rate, pH, biomass level, specific growth rate, oxygen partial pressure ($pO_2$), rate of heat generation, specific by-product production rate, and combinations thereof.

Rate of heat generation can be estimated from the rate of heat removal from chiller data such as chiller flow rate, and/or the inlet and outlet temperature from chiller.

In some embodiments wherein the controlled variable is a by-product concentration, the by-product is selected from the group consisting of isobutyrate, isobutyric acid, dihydroxyisovalerate, ketoisovalerate, isobutyraldehyde, lactate, acetolactate, acetate, formate, glycerol, and combinations thereof.

Specific carbon dioxide evolution rate (CER, millimoles/g/hr) and specific oxygen uptake rate (OUR, millimoles/g/hr) can be calculated by measuring flow rate, inlet and exhaust gas composition of air ($CO_2$, $O_2$ etc.), using, for example, mass spectrometry and/or cell density measurements. Specific carbon dioxide evolution rate is the ratio of carbon dioxide produced (air flow rate multiplied by difference between outlet and inlet carbon dioxide concentration) to cell density per unit time. Specific oxygen uptake rate is the ratio of oxygen consumed (air flow rate multiplied by difference between inlet and outlet oxygen concentration) to cell density. In some embodiments, OUR is measured directly, e.g., using exhaust gas analysis. In some embodiments, CER is measured directly, e.g., using exhaust gas analysis.

In some embodiments, the OUR set point during a biomass growth phase is about 2 to about 10, about 2 to about 9, about 2 to about 8, about 2 to about 7, about 2 to about 6, about 2 to about 5, about 2 to about 4, or about 2 to about 3, about 3 to about 10, about 3 to about 9, about 3 to about 8, about 3 to about 7, about 3 to about 6, or about 3 to about 5 millimoles per grams of cell per hour (mmol/(g cells×h).

In some embodiments, the CER set point during a biomass growth phase is about 1 to about 10, about 1 to about 9, about 1 to about 8, about 1 to about 7, about 1 to about 6, about 1 to about 5.5, about 1 to about 4, about 1 to about 3, about 2.5 to about 10, about 2.5 to about 9, about 2.5 to about 8, about 2.5 to about 7, about 2.5 to about 6, about 2.5 to 5, about 2.5 to about 4, about 2.5 to about 3, about 2 to about 10, about 2 to about 9, about 2 to about 8, about 2 to about 7, about 2 to about 6, about 2 to 5, about 2 to about 4, or about 2 to about 3 mmol/(g cells×h).

Respiratory quotient (RQ) is ratio of CER and OUR. Only the inlet and outlet gas composition from mass spectrometry are required to calculate RQ for a given constant air flow rate. RQ is used as a control variable that couples the oxygen uptake rate with the carbon flux through the bioreactor system. RQ is intrinsically independent of scale. RQ can be measured, for example, using exhaust gas analysis.

Specific growth rate can be estimated from cell density or $OD_{600}$ data or indirectly from OUR data from empirical model.

In some embodiments, the RQ set point during a biomass growth phase is about 0.5 to about 5, about 1 to about 5, about 2 to about 5, about 3 to about 5, about 2 to about 4, about 2 to about 3, about 3 to about 4, about 0.5 to about 5, about 0.7 to about 5, about 0.9 to about 5, about 1.2 to about 5, about 1.4 to about 5, about 1.6 to about 5, about 1.8 to about 5, about 2.2 to about 5, about 2.4 to about 5, about 2.6 to about 5, about 2.8 to about 5, about 3.2 to about 5, about 3.4 to about 5, about 3.6 to about 5, about 3.8 to about 5, about 4.2 to about 5, about 4.4 to about 5, about 4.6 to about 5, about 4.8 to about 5, about 0.5 to about 4, about 0.7 to about 4, about 0.9 to about 4, about 1.2 to about 4, about 1.4 to about 4, about 1.6 to about 4, about 1.8 to about 4, about 2.2 to about 4, about 2.4 to about 4, about 2.6 to about 4, about 2.8 to about 4, about 3.2 to about 4, about 3.4 to about 4, about 3.6 to about 4, about 3.8 to about 4, about 0.5 to about 1.5, about 0.6 to about 1.5, about 0.65 to about 1.5, about 0.67 to about 1.5, about 0.7 to about 1.5, about 0.75 to about 1.5, about 0.8 to about 1.5, about 0.9 to about 1.5, about 0.5 to about 1.2, about 0.6 to about 1.2, about 0.65 to about 1.2, about 0.67 to about 1.2, about 0.7 to about 1.2, about 0.75 to about 1.2, about 0.8 to about 1.2, about 0.9 to about 1.2, about 0.5 to about 1.05, about 0.6 to about 1.05, about 0.7 to about 1.05, about 0.75 to about 1.05, about 0.8 to about 1.05, about 0.9 to about 1.05, about 0.95 to about 1.5, about 0.95 to about 1.4, about 0.95 to about 1.3, about 0.95 to about 1.2, about 0.95 to about 1.1, or about 0.95 to about 1.05.

In certain embodiments, the manipulated variable for increasing biomass is selected from the group consisting of feed rate, feed composition, air flow rate, air composition, stirring rate, pressure, and combinations thereof.

According to the invention, the term "about" includes a deviation of the numerical value of a maximum of 10%, specifically a maximum of 5%, more specifically a maximum of 1%. As an example, the term "about 10 µg" thus defines a range of 9 to 11 µg, specifically 9.5 to 10.5 µg, specifically, 9.9 to 1.1 µg.

The term "production fermentation stage" as used herein refers to the provision of the cultivation conditions wherein lactic acid is produced by the recombinant yeast at a final pH of 3 or less., specifically a final pH of ≤2.9, ≤2.8, ≤2.7, ≤2.6, ≤2.5, ≤2.4, ≤2.3, ≤2.2, ≤2.15 or less may be achieved.

Production fermentation is initiated inoculating yeast cells achieved from seed fermentation into the production reactor. Preferably, the inoculation uses yeast cells with high cell densities, which is >5 g/L, preferably >10 g/L, >20 g/L, >30 g/L, >40 g/L, >50 g/L. Inoculum size may play a significant role in determining the performance of the fermentation.

The cell density of the yeast cells for inoculation or start of fermentation production shall be at least $OD_{600}$ of 3, preferably $OD_{600}$ of about 5, preferably $OD_{600}$ of about 6, preferably $OD_{600}$ of about 7, preferably $OD_{600}$ of about 8, preferably $OD_{600}$ of about 9, more preferably $OD_{600}$ of 10.

The production medium contains high sugar concentrations, specifically glucose sucrose, fructose, maltose, galactose, hydrolysed starch, lactose concentration to ensure high lactic acid titers. The medium is preferably supplemented with nutrients to support cellular metabolism at high sugar, specifically glucose concentrations.

The term "batch culture" refers to a closed culture of microorganisms with growth occurring in a fixed volume of culture medium that is continually being altered by the actions of the growing organisms until it is no longer suitable for growth. In batch culture, all nutrients required for microbial growth are present in the medium before beginning cultivation, except for molecular oxygen in aerobic cultivation.

Batch culture proceeds until complete or almost complete consumption of glucose.

The fermentation media used for seed and lactic acid production fermentation can be a base medium comprising essentially glucose or, as an alternative, sucrose, at least one nitrogen source and water.

The nitrogen source used for the fermentation medium can be, but is not limited to urea, ammonium phosphate, ammonium nitrate, ammonium sulfate.

Furthermore, other salts can be added, such as monopotassium phosphate, magnesium sulfate, copper sulfate, ferric chloride, manganese, sulfate, sodium molybdate, zinc sulfate, biotin, inositol, and thiamine.

Specifically, the base medium can be supplemented by minimal medium salts, selected from $(NH_4)_2SO_4$, $KH_2PO_4$, $MgSO_4.7H_2O$, vitamin solution and trace elements.

Useful vitamin solutions can contain for example D-biotin, Ca-D-pantothenate, Nicotonic acid, Myo-inositol, Thiamine hydrochloride, Pyridoxal hydrochloride and p-aminobenzoic acid.

Useful trace elements can be $Na_2EDTA$, $ZnSO_4.7H_2O$, $MnCl_2.2H_2O$, $CoCl_2.6H_2O$, $CuSO_4.5H_2O$, $Na_2MoO_4.2H_2O$, $CaCl_2.2H_2O$, $FeSO_4.7H_2O$, $H_3BO_3$, KI.

Other fermentation conditions, such as temperature, cell density, selection of substrate(s), selection of nutrients, and the like are generally selected to provide an economical process. A preferred temperature, particularly during the production phase, is from about 25-45° C., specifically about 30° C.

The medium may be buffered or a base may be added to maintain or adjust the pH.

The medium may be buffered or pH may be adjusted by addition of agents during the seed fermentation stage so that the pH is adjusted or maintained in a range of about 3.5 to about 9.0, specifically from about 4.5 to about 7.0, specifically from about 5.0 to about 7.0.

Any suitable buffer known to the skilled person may be used, specifically it is phosphate buffer.

Suitable agents of adjusting the preferred pH are basic materials and include, for example, calcium hydroxide, calcium carbonate, sodium hydroxide, potassium hydroxide, potassium carbonate, sodium carbonate, ammonium carbonate, ammonia, ammonium hydroxide, magnesium hydroxide and the like. Buffering agents that have been used in conventional fermentation processes are also suitable here.

It is preferred to allow the pH of the production fermentation stage to drop from the starting pH that is typically 5.5 or higher, to at or below the pKa of the acid fermentation product, such as in the range from 1.5 to 3.5, specifically in the range of from 1.5 to 3.0, or in the range from 1.5 to 2.5.

Alternatively, the pH of the production fermentation stage is maintained at or below the pKa of lactic acid throughout the process. Therefore, the pH of the fermentation medium is adjusted to at or below the pKa of lactic acid prior to or at the start of the production fermentation process, and is maintained at that level during the production fermentation. In this specific embodiment, the pH is preferably maintained within the range of 1.5 to 3.5, in the range of from 2.0 to 3.0.

In a specific embodiment, the final pH of the production fermentation medium is less than 5, specifically ≤4.5, specifically ≤4, specifically ≤3.5, specifically ≤3, specifically ≤2.5, specifically ≤2.15.

Production fermentation can specifically be performed as a fed-batch process or batch process, batch process being preferred.

According to a specific embodiment, a pH of less than 5, specifically ≤4.5, specifically ≤4, specifically ≤3.5, specifically ≤3, specifically ≤2.5, specifically ≤2.15 is maintained during the whole production fermentation stage.

According to a further specific embodiment, a pH of less than or equal to 3 is maintained during the whole production fermentation stage. In an alternative embodiment, the pH shall be maintained at a pH of ≤2.9, ≤2.8, ≤2.7, ≤2.6, ≤2.5, ≤2.4, ≤2.3, ≤2.2, ≤2.15 or less.

Fermenting, fermentation process or fermentation reaction and like terms as used herein, are intended to encompass both the growth phase and lactic acid biosynthesis phase of the process.

As is described further herein, in some embodiments the bioreactor may comprise a first seed growth reactor and a second fermentation reactor.

The terms "bioreactor" or "fermenter" according to the invention refers to any device or system that supports a biologically active environment and include a fermentation device consisting of one or more vessels and/or towers or piping arrangements. Bioreactors are commonly cylindrical, ranging in size from litres to cubic metres, and are often made of stainless steel, including continuous stirred tank reactor (CSTR), bubble column reactor (BCR), or a trickle bed reactor (TBR), or other vessel or other device suitable for gas-liquid contact. On the basis of mode of operation, a bioreactor may be classified as batch, fed batch or continuous (e.g. a continuous stirred-tank reactor model). An example of a continuous bioreactor is the chemostat.

As mentioned above, seed and production fermentation may be in separate fermenters. Therefore, the bioreactor may comprise a first, seed growth reactor in which the recombinant yeast is cultured, and a second, production fermentation reactor, to which yeast inoculum from the growth reactor is fed and in which most of the lactic acid is produced.

Primary or first or seed fermentation bioreactor as used herein may also encompass one or more reactors that are connected in series of parallel with a secondary, production fermentation bioreactor.

Inoculum density for inoculation of the production fermentation bioreactor preferably is at least $OD_{600}$ of 3.

Secondary production fermentation bioreactor as used herein may encompass any number of further bioreactors that may be connected in series or in parallel with the primary bioreactors. Any one or more of these further bioreactors may also be connected to a further separator.

Recovery of lactic acid from a low pH fermentation medium can be conducted using methods known by the skilled person. Purification can be performed by known techniques, for example by centrifugation, filtration such as microfiltration, ultrafiltration, nanofiltration, liquid-liquid extraction, crystallization, chromatography etc.

In some embodiments, the production fermentation results in lactic acid production of more than 500 mM, preferably more than 60 g/L, more than 80 g/L, more than 100 g/L, more than 120 g/L.

The recombinant yeast strain useful for the method of the invention has lactate dehydrogenase activity due to one or more heterologous LDH genes and further reduced or diminished pyruvate decarboxylase activity.

In this invention, "heterologous" or "foreign" means, with respect to any genetic material, that the genetic material is not native to the host cell.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "mutation" refers to any change or alteration in a nucleic acid sequence. Several types exist, including point, frame shift, and splicing. Mutation may be performed specifically or randomly.

The term "plasmid" refers to a circular, extrachromosomal, optionally self-replicating piece of DNA.

The term "genome" encompasses both the chromosome(s) and plasmids within the recombinant yeast cell.

The term "lactate dehydrogenase" refers to a protein (e.g., enzyme), which catalyses the conversion of pyruvate to lactate.

The term "L-lactate dehydrogenase" refers to an enzyme, which catalyses the conversion of pyruvate to L-lactate, specifically it is classified as EC 1.1.1.27.

The term "D-lactate dehydrogenase" refers to an enzyme, which catalyses the conversion of pyruvate to D-lactate, specifically it is classified as EC 1.1.1.28.

The term "LDH gene" refers to a gene that upon expression yields a protein that has lactate dehydrogenase activity. A LDH gene as used in the present application can include any gene that, when expressed, results in protein having lactate dehydrogenase activity. Lactate dehydrogenase genes can be stereospecific. That is, a lactate dehydrogenase gene may catalyze a reaction to produce only L-lactate or only D-lactate. Other lactate dehydrogenases catalyze a reaction to produce both L- and D-lactate. A L-lactate dehydrogenase gene catalyzes the conversion of pyruvate to L-lactate.

Suitable LDH genes include, but are not limited to those obtained from bacterial, fungal, yeast or mammalian sources. Examples of LDH genes are those obtained from *L.* helveticus, L. casei, B. megaterium, B. stearothermophilus, B. coagulans, L. diolivorans, L. reuteri, Oenococcus oenii, Bos taurus, P. acidilactici, Lactobacillus plantarum, L. johnsonii, L. bulgaricus, L. delbrueckii, L. plantarum and L. pentosus. Preferably, the coded LDH enzyme is fructose bisphosphate independent, such as the L-LDH from L. plantarum.

Examples of specific L-LDH genes are those obtained from Lactobacillus plantarum, L. helveticus, L. casei, B. megaterium, B. stearotherm, B. taurus, P. acidilactici, and human or bovine sources.

Examples of specific D-LDH genes are those obtained from L. helveticus, L. johnsonii, L. bulgaricus, L. delbrueckii, L. plantarum and L. pentosus.

Functional genes that are identical or at least 80%, 85%, 90% or 95% homologous to any of these L-LDH or D-LDH genes are suitable. The native genes obtained from any of these sources may be subjected to mutagenesis if necessary to provide a coding sequence starting with a eukaryotic starting codon (ATG).

Percent identity of DNA, RNA or other genetic material and of protein amino acid sequences can be computed conveniently using BLAST or SmartBLAST software with default parameters.

The recombinant yeast cells may contain a single LDH gene or multiple LDH genes, such as from 1 to 10 LDH genes, especially from 1 to 5 LDH genes. When the transformed yeast contains multiple LDH genes, the individual genes may be copies of the same gene, or include copies of two or more different LDH genes. Multiple copies of the exogenous LDH gene may be integrated at a single locus, so they are adjacent each other, or at several loci within the yeast genome.

The exogenous LDH gene is under the transcriptional control of one or more promoters and one or more terminators, both of which are functional in the modified yeast cell.

As used according to the invention, the term "promoter" refers to an untranscribed sequence located upstream (i.e., 5') to the translation start codon of a structural gene (generally within about 1 to 1000 bp, preferably 1-500 bp, especially 1-100 bp) and which controls the start of transcription of the structural gene.

The term "termination sequence" refers to an untranscribed sequence located downstream (i.e., 3') to the translation finish codon of a structural gene (generally within about 1 to 1000 bp, more typically 1-500 base pairs and especially 1-100 base pairs) and controls the end of transcription of the structural gene.

A promoter or terminator is "operatively linked" to a structural gene if its position in the genome relative to that of the structural gene is such that the promoter or terminator, as the case may be, performs its transcriptional control function.

Promoter and terminator sequences may be native or exogenous to the recombinant yeast cell of the invention. Particularly suitable LDH genes include those that encode for an enzyme with an amino acid sequence that has an identities score of at least 60%, especially at least 80%, 85% or 95%, compared with UniProtKB—P56512 (LDH1_LACPL), SEQ ID No. 1:

```
MSSMPNHQKVVLVGDGAVGSSYAFAMAQQGIAEEFVIVDVVKDRTKGDAL

DLEDAQAFTAPKKIYSGEYSDCKDADLVVITAGAPQKPGESRLDLVNKNL
```

-continued
```
NILSSIVKPVVDSGFDGIFLVAANPVDILTYATWKFSGFPKDRVIGSGTS

LDSSRLRVALGKQFNVDPRSVDAYIMGEHGDSEFAAYSTATIGTRPVRDV

AKEQGVSDEDLAKLEDGVRNKAYDIINLKGATFYGIGTALMRISKAILRD

ENAVLPVGAYMDGQYGLNDIYIGTPAVIGGTGLKQIIESPLSADELKKMQ

DSAATLKKVLNDGLAELENK.
```

The use of native yeast cell promoters and terminators, together with respective upstream and downstream flanking regions, can permit the targeted integration of the LDH gene into specific loci of the yeast genome, and for simultaneous integration the LDH gene and deletion or disruption of another native gene, such as, for example, a PDC gene.

When multiple exogenous LDH genes are introduced into the yeast cell, it is possible for the different LDH genes to be under the control of different types of promoters and/or terminators.

The exogenous LDH gene may be integrated randomly into the yeast genome or inserted at one or more targeted locations. Examples of targeted locations include the locus of one or more genes that are desirably deleted or disrupted, such as that of a PDC or MTH1 gene.

The terms "deletion" and "disruption", refer to the elimination of the entire coding region of the gene, or modification of the respective promoter and/or terminator region such as by deletion, insertion or mutation so that the gene either does not express the protein or an active version of the protein, or produces an enzyme with significantly reduced activity. The deletion or disruption can be accomplished by genetic engineering methods, forced evolution or mutagenesis, followed by appropriate selection or screening to identify the desired mutants.

The recombinant yeast of the invention further has additional genetic modifications of the PDC1, PDC5 and/or PDC6 genes, e.g. a deletion or disruption thereof, thereby reducing the yeast's ability to produce ethanol.

PDC1 and PDC5 are active during glucose fermentation where PDC1 is expressed about six times more strongly than PDC5. Expression of PDC6 is weak and seems to be induced in ethanol medium.

Specifically the recombinant yeast is a pyruvate decarboxylase negative or inactive or reduced yeast strain that has reduced or no detectable pyruvate decarboxylase activity, and that does not grow or shows impaired growth in an aerobic environment on glucose as a sole carbon source in a synthetic culture medium and may not produce detectable amounts of ethanol (e.g., less than about 1 ppm) during growth in an aerobic environment in a minimal medium.

Specifically, one, two or all of PDC1, PDC5 and PDC6 genes are functionally knocked out or deleted. Specifically, the recombinant yeast strain lacks both alleles of PDC1, PDC5 and PDC6.

Alternatively, one, two or all of PDC1, PDC5 and PDC6 genes are conditionally expressed due to control of constitutive conditional/inducible promoters, i.e. promoters which down-regulate or up-regulate gene expression under certain conditions or upon addition of selected supplements. In a specific embodiment, the conditional promoters are glucose repressible. In another specific embodiment, the conditional promoters are pH dependent, preferably active at a pH of >5, but inactive at a pH of <4. In a specific embodiment, the conditional promoters are from HXT genes, specifically from HXT2, HXT4, HXT1 or HXT7.

Examples of suitable constitutive promoters are promoters from glycolytic enzymes. Examples for such glycolytic promoters are the TPI1 (triose phosphate isomerase 1 promoter, the TDH3 (GAPH, glyceraldehyde-3-phosphate dehydro-genase) promoter, the PGK1 (3-phosphoglycerate kinase) promoter and the PGI1 phosphoglucose isomerase) promoter.

Saccharomyces cerevisiae has 20 genes that encode proteins similar to glucose (hexose) transporters (HXT1 to HXT17, GAL2, SNF3, and RGT2). These Hxt proteins belong to the major facilitator superfamily (MFS) of transporters. MFS proteins transport their substrates by passive, energy-independent facilitated diffusion, with glucose moving down a concentration gradient. The hexose transporter genes are HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3 and RGT2, however any other yet unknown gene encoding a hexose transport system useful in yeast is encompassed herein as well.

According to one embodiment, one or more of the above listed hexose transporter genes are overexpressed using heterologous constitutive or inducible promoters.

According to a further embodiment, the yeast comprises a functional deletion of the MTH1 or STD1 gene. According to a further embodiment, the yeast comprises overexpression of the MTH1 gene The Std1 protein modulates the expression of glucose-regulated genes and is supposed to interact with the glucose sensors, Snf3 and Rgt2. The homologue of Std1, Mth1, is assumed to interact with Snf3 but not Rgt2. Genetic interactions between STD1, MTH1, SNF3, and RGT2 suggest that the glucose signalling is mediated, at least in part, through interactions of the products of these genes. In media lacking glucose or with low levels of glucose, the hexose transporter genes are subject to repression by a mechanism that requires the Std1 and Mth1 proteins.

According to a specific embodiment of the invention, the MTH1 gene comprises at least a partial deletion resulting in lack of functionality of the gene expression product.

Specifically useful for the method described herein is a recombinant diploid yeast strain, preferably Saccharomyces cerevisiae, comprising functional deletion of PDC1, PDC5 and PDC6 genes, functional deletion of MTH1 gene, overexpression of HXT1 gene, and at least one heterologous LDH gene.

As used herein, the term "haploid" refers to haploid yeast cells having one copy of each chromosome, i.e. a single set of unpaired chromosomes.

As used herein, the term "diploid" refers to diploid yeast cells having two homologous copies of each chromosome. In a diploid state the haploid number is doubled, thus, this condition is also known as 2n.

"Homologous chromosomes" or "homologous copies of each chromosome" means that the chromosomes have the same genes in the same loci where they provide points along each chromosome which enable a pair of chromosomes to align correctly with each other. However, the chromosomes (and genes) are not necessarily identical. The same gene can be coded by two different alleles. An allele is the variant form of a given gene.

Polyploidy refers to cells containing more than two paired homologous sets of chromosomes, i.e. it refers to a numerical change in a whole set of chromosomes. Polyploidy is the state where cells have multiple sets of chromosomes beyond the basic set, usually 3 or more.

Aneuploidy is the presence of an abnormal number of chromosomes in a cell, e.g. a state where one or more chromosomes of a normal set are missing or present in more than their usual number of copies. Unlike euploidy, aneuploid karyotypes are not a multiple of the haploid number. Aneuploidy describes also the state in which significant parts of one or more chromosomes are missing or present in more than their usual number of copies.

The diploid yeast cells as described herein are capable of producing free lactic acid at an amount of 80 g/100 g glucose or more at a very low pH, i.e. even lower than 2.5.

The present invention encompasses following items:

1. A method for producing lactic acid in a recombinant yeast cell culture using a sugar, specifically glucose or sucrose as carbon source comprising
   a) a seed fermentation stage to produce biomass wherein the yeast is cultivated in a culture medium at a pH of 5 to 7, followed by
   b) a production fermentation stage with biomass from the seed fermentation to produce lactic acid, wherein the yeast is cultivated in a culture medium at a pH of <5, and
   wherein said yeast has lactate dehydrogenase (LDH) activity and/or decreased pyruvate decarboxylase (PDC) activity.

2. The method according to item 2, wherein the yeast cell is a diploid, polyploid or aneuploid cell, specifically said yeast cell is selected under stress conditions and genetically modified.

3. The method according to item 1 or 2, wherein seed fermentation is at high glucose concentration.

4. The method according to items 1 to 3, wherein production fermentation is at low glucose concentration.

5. The method according to any one of items 1 to 4, wherein lactic acid is purified by common industrial processes.

6. The method according to any one of items 1 to 5, wherein lactic acid is purified from the fermentation stage with a purity of at least 90%.

7. The method according to any one of items 1 to 6, wherein the production fermentation stage is at a pH of <4.5, specifically <4, specifically <3.5.

8. The method according to any one of items 1 to 7, wherein the production fermentation stage has a final pH of 3 or less, specifically a final pH of ≤2.9, ≤2.8, ≤2.7, ≤2.6, ≤2.5, ≤2.4, ≤2.3, ≤2.2, ≤2.15 or less.

9. The method according to any one of items 1 to 8, wherein the seed fermentation stage is performed under fed-batch conditions.

10. The method according to any one of items 1 to 9, wherein the production fermentation stage is performed under batch process conditions.

11. The method according to any one of items 1 to 10, wherein the seed fermentation stage and the production fermentation stage are in separate fermenters.

12. The method according to any one of items 1 to 11, wherein lactic acid is produced in free form, specifically it is produced in optically pure isomeric form, specifically it is either D(−) or L(+)-lactic acid.

13. The method according to any one of items 1 to 12, wherein the yeast has decreased or knocked out expression of one or more of the genes PDC1, PDC5 and/or PDC6.

14. The method according to any one of item 13 wherein one or more of promotors of PDC1, PDC5 and/or PDC6 genes are substituted or deleted.

15. The method according to item 14, wherein the genes PDC1, PDC5 and/or PDC6 are conditionally expressed, specifically due to the control of heterologous promoters, specifically glucose repressible promoters, more specifically due to the control of HXT2 or HXT4 gene promoters.

16. The method of according to any one of items 13 to 15, wherein the at least one of the genes PDC1, PDC5 and/or PDC6 is deleted.

17. The method according to any one of items 1 to 16, wherein the yeast has decreased or knocked-out expression of one or more genes encoding proteins interacting with glucose sensors controlling glucose-regulated gene expression, specifically expression of Std1 or Mth1 proteins.

18. The method according to any one of items 1 to 17, wherein the MTH1 gene is partially or completely deleted.

19. The method of any one of items 1 to 18, wherein the yeast is modified to overexpress at least one hexose transporter gene.

20. The method of any one of items 1 to 19, wherein the yeast is modified to overexpress at least one of hexose transporter genes selected from the group of HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3 and RGT2.

21. The method according to any one of items 1 to 20, wherein the initial concentration of glucose in the production stage is at least 10% (w/w), specifically 20% (w/w) or more, more specifically 25% or more.

22. Recombinant yeast comprising one or more heterologous lactate dehydrogenase (LDH) genes and having decreased pyruvate decarboxylase (PDC).

23. The recombinant yeast according to item 22, which has decreased or knocked out expression of one or more of the genes encoding PDC1, PDC5 and/or PDC6.

24. The recombinant yeast according to item 23, wherein one or more of promotors of PDC1, PDC5 and/or PDC6 genes are substituted or deleted.

25. The recombinant yeast according to item 23 or 24, wherein the genes encoding PDC1, PDC5 and/or PDC6 are conditionally expressed, specifically due to the control of heterologous promoters, specifically glucose repressible promoters, more specifically due to the control of HXT2 or HXT4 gene promoters.

26. The recombinant yeast according to item 23 to 25, wherein the at least one of the genes encoding PDC1, PDC5 and/or PDC6 is deleted.

27. The recombinant yeast according to any one of items 23 to 26, having decreased or knocked-out expression of one or more genes encoding proteins interacting with glucose sensors controlling glucose-regulated gene expression, specifically expression of Std1 or Mth1 proteins.

28. The recombinant yeast according to any one of items 23 to 27, wherein the MTH1 gene is partially or completely deleted.

29. The recombinant yeast according to any one of items 23 to 28, which is modified to overexpress at least one hexose transporter gene.

30. The recombinant yeast according to any one of items 23 to 29, which is modified to overexpress at least one of hexose transporter genes selected from the group of HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3 and RGT2.

31. Recombinant yeast strain, specifically diploid, polyploid or aneuploid yeast cells, comprising
   i) functional deletion of PDC1, PDC5 and PDC6 genes,
   ii) functional deletion of MTH1 gene,
   iii) overexpression of HXT1 gene, and
   iv) heterologous expression of LDH gene 32. The recombinant yeast strain of any one of items 23 to 31, which is of the species Saccharomyces cerevisiae.

33. Two step fermentation system for producing lactic acid with glucose as carbon source using a recombinant yeast strain, consisting of
   a) a seed fermentation stage to produce biomass, wherein the yeast cells are cultivated in a culture medium at a pH of 5 to 7, followed by
   b) a production fermentation stage to produce lactic acid, wherein the yeast cells are cultivated in a cell culture medium until a final pH of 3.5. or less, specifically a pH of $\leq 3.4$, $\leq 3.3$, $\leq 3.2$, $\leq 3.1$, $\leq 3.0$, $\leq 2.9$, $\leq 2.8$, $\leq 2.7$, $\leq 2.6$, $\leq 2.5$, $\leq 2.4$, $\leq 2.3$, $\leq 2.2$, $\leq 2.15$ or less is reached.
   wherein the yeast encodes a heterologous lactate dehydrogenase (LDH) and has decreased pyruvate decarboxylase (PDC) activity.

34. Two stage fermentation system for producing lactic acid with glucose as carbon source using a recombinant yeast strain, consisting of
   a) a seed fermentation stage in a first fermenter to produce biomass, wherein the yeast cells are cultivated in a cell culture medium at a pH of 5 to 7, followed by
   b) a production fermentation in a second fermenter stage inoculated from the seed fermentation to produce lactic acid, wherein the yeast cells are cultivated in a cell culture medium at a pH of less than 3.5, specifically a pH of $\leq 2.9$, $\leq 2.8$, $\leq 2.7$, $\leq 2.6$, $\leq 2.5$, $\leq 2.4$, $\leq 2.3$, $\leq 2.2$, $\leq 2.15$ or less,
   wherein the yeast is modified to have lactate dehydrogenase (LDH) activity and/or decreased pyruvate decarboxylase (PDC) activity.

35. Combination of two or more fermenter systems for producing lactic acid with glucose as carbon source using a recombinant yeast strain, consisting of
   a) a seed fermenter to produce biomass, wherein the yeast cells are cultivated in a cell culture medium at a pH of 5 to 7, followed by
   b) a production fermenter inoculated from the seed fermentation to produce lactic acid, wherein the yeast cells are cultivated in a cell culture medium at a pH of less than 3.5, specifically a pH of $\leq 3.4$, $\leq 3.3$, $\leq 3.2$, $\leq 3.1$, $\leq 3.0$, $\leq 2.9$, $\leq 2.8$, $\leq 2.7$, $\leq 2.6$, $\leq 2.5$, $\leq 2.4$, $\leq 2.3$, $\leq 2.2$, $\leq 2.15$ or less,
   wherein the yeast is encodes a heterologous lactate dehydrogenase (LDH) gene and has a decreased pyruvate decarboxylase (PDC) and.

EXAMPLES

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

If not indicated otherwise, the yeast cells used in the examples are diploid yeast cells.

Example 1: Characterization of S. cerevisiae (CBS7962) Strain for Fermentation Performance at Different Glucose and Lactic Acid Concentrations and pH The S. cerevisiae CBS7962 strain was cultivated in bioreactors and in shake flasks in two stages. An inoculum development stage with a medium containing 1.8 g/l of YNB, 5 g/l of $(NH_4)_2SO_4$ and 20 g/l of glucose was used. Cells from glycerol vials stored at −80° C. were used to inoculate a 50 ml of preinoculum medium at an optical density at 600 nm (OD600) of 0.05. After 24 h of growth, the cells were harvested and used as inoculum in cultivation stage in shake flasks and in bioreactors (Eppendorf DASGIP DASbox 4, Germany) with a working volume of 50 ml and 700 ml, respectively. The medium composition and fermentation parameters in the cultivation stage are listed in Table 1 and Table 2. All cultivations were performed at 30° C.; shake flasks were incubated in an orbital shaker set at 180 rpm; pH in shake flasks were maintained at 3.0 by adding potassium hydrogen phthalate buffer to a concentration of 100 mM; pH in bioreactor cultivations were maintained by automatic addition of 2M NaOH. The bioreactor cultivations were programmed to maintain the dissolved oxygen concentration of 20% and above by controlling the aeration and stirrer speed. Samples were withdrawn from the shake flask and bioreactor cultivations at regular intervals to measure growth by following the optical density at 600 nm and to measure the supernatant for metabolites including glucose, ethanol, glycerol and lactic acid using an Aminex HPX-87H column set in a HPLC (Shimadzu scientific instruments) at 60° C., and 5 mM $H_2SO_4$ as an eluant with a flow rate of 0.6 ml/min. Results clearly show that the fermentation rates and yields for ethanol production, at high concentrations of glucose and in the presence of lactic acid in the medium, can be significantly improved by increasing the concentrations of YNB and ammonium sulfate and by increasing the initial inoculum size (Table1 and Table2).

kanamycin and hygromycin as selectable markers. The primer sequences for deletion and verification primers are listed in the table 3. Two constructs were designed for deletion of one of the alleles. Each construct contained a flank of the target gene followed by a LoxP site and roughly one half of one of the selectable markers. The flank region and LoxP sites were included in the primer that was used to amplify parts of selectable markers of kanamycin and hygromycin from pPM2aK21 and pPM2a_hphR, respectively. Two PCR constructs containing flank regions of the target gene, LoxP site and parts of one of the selectable markers were transformed into CBS7962 strain. The transformation was carried out according to the LiAc/PEG/ss-DNA protocol (http://home.cc.umanitoba.ca/~gietz/method.html). The transformants were plated on selective YP ethanol-glycerol medium (10 g/l of yeast extract, 20 g/l of peptone, 10 g/l of ethanol and 10 g/l of glycerol) and incubated for 3-4 days at 30° C. Single colonies were then subjected to colony PCR using verification primers for the target gene. Colony PCR was performed as follows: a yeast colony was gently touched using a pipette tip and transferred to a PCR tube containing 1.2M of sorbitol, 100 mM of sodium hydrogen phosphate and 1500 U/ml of lyticase enzyme and incubated at 37° C. for 15 min; a PCR was performed using verification primers of the target gene and the lysed cell suspension as a template. A yeast colony that was verified to have lost one allele of a pdc gene was used for transformation to knockout the other allele of the target gene using two PCR constructs containing flank regions of the target gene, LoxP site and parts of other selectable marker. Those transfor-

TABLE 1

Bioreactor cultivations of *S. cerevisiae* CBS7962

| YNB, g/l | $(NH_4)_2SO_4$, g/l | Glucose, g/l | pH | Initial inoculum, OD600 nm | Ethanol yield, g/g | Max. Ethanol productivity, g/l/h | Lactic acid in medium, g/l |
|---|---|---|---|---|---|---|---|
| 1.8 | 5 | 20 | 5 | 0.1 | 0.40 | 0.55 | — |
| 1.8 | 5 | 20 | 3 | 0.1 | 0.40 | 0.45 | — |
| 1.8 | 5 | 125 | 5 | 0.1 | 0.36 | 0.92 | — |
| 1.8 | 5 | 250 | 5 | 0.1 | 0.32 | 0.47 | — |
| 1.8 | 5 + 5* | 125 | 5 | 0.1 | 0.37 | 1.48 | — |
| 3.6 | 10 | 125 | 5 | 0.1 | 0.41 | 2.60 | — |
| 3.6 | 10 | 250 | 5 | 0.1 | 0.40 | 3.78 | — |
| 3.6 | 10 | 250 | 3 | 0.1 | 0.40 | 2.83 | — |
| 3.6 | 10 | 250 | 3 | 0.1 | 0.37 | 0.40 | 15 |
| 3.6 | 10 | 250 | 5 | 0.1 | 0.40 | 3.03 | 15 |

TABLE 2

Shake flask cultivations of *S. cerevisiae* CBS7962

| YNB + $(NH_4)_2SO_4$, g/l | Glucose, g/l | pH | Initial inoculum, OD600 nm | Ethanol yield, g/g | Ethanol productivity at 30 h, g/l/h | Lactic acid in medium, g/l |
|---|---|---|---|---|---|---|
| 3.6 + 10 | 125 | 3 | 0.5 | 0.38 | 0.53 | 15 |
| 3.6 + 10 | 125 | 3 | 1.0 | 0.38 | 0.97 | 15 |
| 3.6 + 10 | 125 | 3 | 2.0 | 0.38 | 1.35 | 15 |

Example 2: Construction of *S. cerevisiae* Strain Lacking Pyruvate Decarboxylase (PDC1, PDC5 and PDC6) Genes Using Split-Maker Deletion Method Knockout of both the alleles of PDC1, PDC5 and PDC6 was facilitated by the split-maker deletion method with mants that appear on YP ethanol-glycerol medium containing G418 and hygromycin plate were verified using colony PCR for deletion of both the alleles of target gene. The resulting strain with one of the three pdc genes deleted was transformed with a CRE plasmid to remove both the selectable markers. The strains expressing CRE plasmid was later grown on non-selective YP ethanol-glycerol plate to obtain colonies without CRE plasmid. The yeast strain with one of the pdc genes deleted was then used to knockout other pdc genes using the same procedure described above.

TABLE 3

Primer sequences of PDCs deletion and verification primers

| Component name | Sequence, 5' to 3' |
|---|---|
| PDC1 deletion primer, upstream | CAAAATGCATAACCTATGCATTTAAAAGATTATGTATGCTCTTCTGACTTTTCG (SEQ ID No. 2) |
| PDC1 deletion primer, downstream | TAAGTGACAGTGCAGTAATAATATGAACCAATTTATTTTTCGTTACATAAAAATGC (SEQ ID No. 3) |
| PDC5 deletion primer, upstream | CATTATTTTAATTTTTTTTCTATTACTGTCGCTAACACCTGTATGGTTG (SEQ ID No. 4) |
| PDC5 deletion primer, downstream | GCATATTAATAGTATACAACAAAAACAAAGGAAAAAAGAAATGAAATC (SEQ ID No. 5) |
| PDC6 deletion primer, upstream | CTATGTACTTGGCAATAGATGAGCATTTCAATGAAGGAAACGCCTGAGTCAGTTATG (SEQ ID No. 6) |
| PDC6 deletion primer, downstream | GGGCGGCGTCCCCTGTTTTCTGCTTTGGCTCATCTCTTTGGCTCCGACGGACGAAAG (SEQ ID No. 7) |
| PDC1 verification primer_fw | AAGGCTCTTTCACTCTCCTTGC (SEQ ID No. 8) |
| PDC1 verification inner primer_bw | TTAGCGGCGTCAGCAATAGTGG (SEQ ID No. 9) |
| PDC1 verification inner primer_fw | CCACTATTGCTGACGCCGCTAA (SEQ ID No. 10) |
| PDC5 verification primer_fw | TCGCTAACACCTGTATGGTTGC (SEQ ID No. 11) |
| PDC5 verification inner primer_bw | CTTGACATCATGTCTAGAAGC (SEQ ID No. 12) |
| PDC5 verification inner primer_fw | TTCTAGACATGATGTCAAGGC (SEQ ID No. 13) |
| PDC5 verification inner primer_bw | ACTAAGTGACAAAGAACTACGC (SEQ ID No. 14) |
| PDC6 verification primer_fw | TACAGTCGGTAATTTCTTTCTGG (SEQ ID No. 15) |
| PDC6 verification inner primer_bw | GGATCAAATCAGCCGACTCAACG (SEQ ID No. 16) |
| PDC6 verification inner primer_fw | CGTTGAGTCGGCTGATTTGATCC (SEQ ID No. 17) |
| PDC6 verification inner primer_bw | TAAAGCTGTAAGCTAGACCACC (SEQ ID No. 18) |

Example 3: Construction of S. cerevisiae Strain with Inactive Pyruvate Decarboxylase (PDC1, PDC5 and PDC6) Genes: Knock-Out of Pdc Genes Using CRISPR-Cas9 System CRISPR-cas9 system, a RNA guided endonuclease activity to induce double stranded DNA breaks (dsb) at the target site and repairing the dsb with double stranded (ds) DNA homology oligos containing stop codons is used to inactivate pdc genes. Transformations are carried out according to LiAc/PEG/ss-DNA protocol (http://home.cc.umanitoba.ca/~gietz/method.html). The endonuclease enzyme, cas9, is constructed in a centromeric plasmid under TEF1 promoter and CYC1 terminator using golden gate assembly (Engler et al., 2008). The guide RNAs (gRNA) for PDC1, PDC5 and PDC6 genes are identified using ChopChop (https://chopchop.rc.fas.harvard.edu/). The 20 bp gRNA is constructed to contain a sequence of hammer head (HH) ribozyme and a sequence of hepatitis delta virus (HDV) ribozyme on 5' and 3' ends, respectively (Table 4). The ribozyme-gRNA-ribozyme (RGR) construct is obtained using PCR with overlapping primers (Table 4). PCR for constructing RGR is performed using four common overlapping primers including 1gRNA_all_rev, 2gRNA_all_rev, 3gRNA_all_rev and 4gRNA_all_fw and two forward primers specific for gRNAs of pdc genes (Table 4). Using golden gate assembly, the RGR construct is assembled in a 2µ plasmid with TPI1 promoter and CYC1 terminator. The dsDNA oligos used for assisting the repair of dsb is PCR constructed to contain a stop codon which is flanked by about 90 bp homology region on both the ends. Knock-out of pdcs, one gene at a time, is carried out in two steps. In the first step, a yeast strain expressing cas9 is obtained by transforming the centromeric plasmid, containing cas9, into CBS7962 strain. The cas9 expressing strain is transformed with PDC1 RGR plasmid and its respective dsDNA oligos. The transformants are plated on selective YPD medium (10 g/l of yeast extract, 20 g/l of peptone and 20 g/l of glucose) and incubated for 3-4 days at 30° C. Single colonies are verified for PDC1 knock-out using PCR. To this end the presence of the PDC gene is verified by amplification with suitable primers. The PDC1 knock-out strain containing the centromeric cas9 plasmid is used to knock-out two other PDC genes using the same procedure described above. For the last PDC knock-out transformants are plated on selective YP ethanol-glycerol medium (10 g/l of yeast extract, 20 g/l of peptone, 10 g/l of ethanol and 10 g/l of glycerol) to enable growth of these knock-out strains.

TABLE 4 gRNA sequence, primer sequence and gRNA construct sequence for PDCs inactivation using CRISPR-Cas9

| Component name | Sequence, 5' to 3' |
|---|---|
| gRNA, PDC1 | GATACGAGCGTAACCATCAG (SEQ ID No. 19) |
| gRNA, PDC5 | TGAAGTCAAAGGTATGAGAT (SEQ ID No. 20) |

TABLE 4 -continued gRNA sequence, primer sequence and gRNA construct sequence for PDCs inactivation using CRISPR-Cas9

| Component name | Sequence, 5' to 3' |
| --- | --- |
| gRNA, PDC6 | GTAACCATCGGCGGCATAGG (SEQ ID No. 21) |
| Primer for gRNA construct, 1_PDC1_A_fw | CATGCGTATCCTGATGAGTCCGTGAGGACGAAA CGAGTAAGCTCGTCGATA (SEQ ID No. 22) |
| Primer for gRNA construct, 2_PDC1_A_fw | AAACGAGTAAGCTCGTCGATACGAGCGTAACCA TCAGgttttagagctagaaatagcaag (SEQ ID No. 23) |
| Primer for gRNA construct, 1_PDC5_A_fw | CATGACTTCACTGATGAGTCCGTGAGGACGAAA CGAGTAAGCTCGTCTGAA (SEQ ID No. 24) |
| Primer for gRNA construct, 2_PDC5_A_fw | AAACGAGTAAGCTCGTCTGAAGTCAAAGGTATGA GATgttttagagctagaaatagcaag (SEQ ID No. 25) |
| Primer for gRNA construct, 1_PDC6_A_fw | CATGGGTTACCTGATGAGTCCGTGAGGACGAAA CGAGTAAGCTCGTCGTAA (SEQ ID No. 26) |
| Primer for gRNA construct, 2_PDC6_A_fw | AAACGAGTAAGCTCGTCGTAACCATCGGCGGCA TAGGgttttagagctagaaatagcaag (SEQ ID No. 27) |
| Overlapping primer, 4gRNA_all_fw | Gttttagagctagaaatagcaagttaaaataaggctagtccgt tatcaacttgaaaaagt (SEQ ID No. 28) |
| Overlapping primer, 1gRNA_all_rev | CGCCATGCCGAAGCATGTTGCCCAGCCGGCGC CAGCGAGGAGGCTGGGACCATGCCGGCC (SEQ ID No. 29) |
| Overlapping primer, 3gRNA_all_rev | AGGCTGGGACCATGCCGGCCaaaagcaccgactcggt gccacttttttcaagttgataacg (SEQ ID No. 30) |
| Overlapping primer, 2gRNA_all_rev | AAGCAGTCCAAAGCTGTCCCATTCGCCATGCCG AAGCATGTTGCCCAGCCG (SEQ ID No. 31) |
| gRNA construct: HH ribozyme-pdc1gRNA-HDV ribozyme with golden gate fusion sites | CATGCGTATCCTGATGAGTCCGTGAGGACGAAA CGAGTAAGCTCGTCGATACGAGCGTAACCATCA Ggttttagagctagaaatagcaagttaaaataaggctagtccg ttatcaacttgaaaaagtggcaccgagtcggtgcttttGGCCG GCATGGTCCCAGCCTCCTCGCTGGCGCCGGCTGGGCAA CATGCTTCGGCATGGCGAATGGGACAGCTTTGG ACTGCTT (SEQ ID No. 32) |
| gRNA construct: HH ribozyme-pdc5gRNA-HDV ribozyme with golden gate fusion sites | CATGACTTCACTGATGAGTCCGTGAGGACGAAA CGAGTAAGCTCGTCTGAAGTCAAAGGTATGAGAT gttttagagctagaaatagcaagttaaaataaggctagtccgt tatcaacttgaaaaagtggcaccgagtcggtgcttttGGCCGG CATGGTCCCAGCCTCCTCGCTGGCGCCGGCTGGGCAACAT GCTTCGGCATGGCGAATGGGACAGCTTTGGACT GCTT (SEQ ID No. 33) |
| gRNA construct: HH ribozyme-pdc6gRNA-HDV ribozyme with golden gate fusion sites | CATGGGTTACCTGATGAGTCCGTGAGGACGAAA CGAGTAAGCTCGTCGTAACCATCGGCGGCATAG Ggttttagagctagaaatagcaagttaaaataaggctagtccg ttatcaacttgaaaaagtggcaccgagtcggtgcttttGGCCG GCATGGTCCCAGCCTCCTCGCTGGCGCCGGCTGGGCAA CATGCTTCGGCATGGCGAATGGGACAGCTTTGG ACTGCTT (SEQ ID No. 34) |
| dsDNA oligo with stop codons, for PDC1 inactivation | AACTTGTCCTTGTTGGACAAGATCTACGAAGTTG AAGGTATGAGATGGGCTGGTAACGCCAACGAAT TGAACGCTGCTTACGCtGCTGattgaATGGTTACGC TCGATCAAGGGTATGTCTTGTATCATCACCACCT TCGGTGTCGGTGAATTGTCTGCTTTGAACGGTAT TGCCGGTTC (SEQ ID No. 35) |
| dsDNA oligo with stop codons, for PDC5 inactivation | TGTCTGCCAACATTTCTGAAACCACTGCCATGAT CACTGATATTGCTAACGCTCCAGCTGAAATTGAC AGATGTATCAGAaCACCTactagACACTACCCAA GACCAGTCTACTTGGGTTTGCCAGCTAACTTGGT TGACTTGAACGTCCCAGCCAAGTTATTGGAAACT CCAATTGAC (SEQ ID No. 36) |

TABLE 4 -continued

| gRNA sequence, primer sequence and gRNA construct sequence for PDCs inactivation using CRISPR-Cas9 | |
|---|---|
| Component name | Sequence, 5' to 3' |
| dsDNA oligo with stop codons, for PDC6 inactivation | CAGGCGACTTCAACTTGTCCCTATTGGACAAGAT TTACGAGGTAGATGGATTGAGATGGGCTGGTAA TGCAAATGAGCTGAACGaCGCCTattgaATGCCGC CGATGGTACGCACGCATCAAGGGTTTATCTGTG CTGGTAACTACTTTTGGCGTAGGTGAATTATCCG CCTTGAATGGT (SEQ ID No. 37) |

Example 4: Construction of *S. cerevisiae* (CBS7962) Strain Auxotrophs for Uracil, Tryptophan and Histidine: Inactivation of URA3, TRP1 and HIS3 Genes Using CRISPR-Cas9 System CRISPR-cas9 system, a RNA guided endonuclease activity to induce double stranded DNA breaks (dsb) at the target site and repairing the dsb with double stranded (ds) DNA homology oligos containing stop codons were used to inactivate URA3, TRP1 and HIS3 genes. Transformations were carried out according to LiAc/PEG/ss-DNA protocol (http://home.cc.umanitoba.ca/~gietz/method.html). The endonuclease enzyme, cas9, was constructed in a centromeric plasmid under TEF1 promoter and CYC1 terminator using golden gate assembly (Engler et al., 2008). The guide RNAs (gRNA) for URA3, TRP1 and HIS3 genes were identified using ChopChop (https://chopchop.rc.fas.harvard.edu/). The 20 bp gRNA was constructed to contain a sequence of hammer head (HH) ribozyme and a sequence of hepatitis delta virus (HDV) ribozyme on 5' and 3' ends, respectively (Table 5). The ribozyme-gRNA-ribozyme (RGR) construct was obtained using PCR with overlapping primers. PCR for constructing RGR is performed using four common overlapping primers including 1gRNA_all_rev, 2gRNA_all_rev, 3gRNA_all_rev and 4gRNA_all_fw and two forward primers specific for gRNAs of URA3, TRP1 and HIS3 genes (Table 5). Using golden gate assembly, the RGR construct was assembled in a 2µ plasmid with TPI1 promoter and CYC1 terminator. The dsDNA oligos used for assisting the repair of dsb was PCR constructed to contain two stop codons which was flanked by approximately 40-50 bp homology region on both the ends (Table 5). Knock-out of URA3, TRP1 and HIS3 genes, one gene at a time, was carried out in two steps. In the first step, a yeast strain expressing cas9 was obtained by transforming the centromeric plasmid, containing cas9, into CBS7962 strain. The cas9 expressing strain was transformed with URA3 RGR plasmid and its respective dsDNA oligo. The transformants were plated on selective YPD medium (10 g/l of yeast extract, 20 g/l of peptone and 20 g/l of glucose) and incubated for 3-4 days at 30° C. Single colonies were then replica plated on YNB-uracil-FOA medium (1.8 g/l of YNB, 5 g/l of (NH4)2SO4, 20 g/l of glucose, 1 g/l of 5'FOA and 500 µg/ml of uracil) and YNB dropout medium (1.8 g/l of YNB, 5 g/l of (NH4)2SO4 and 20 g/l of glucose). The URA3 knock-out strain with cas9 expressing plasmid was subjected to stepwise knock-out of TRP1 and HIS3 genes using the same procedure described above.

TABLE 5

| Sequences of gRNA, primers, dsDNA oligos and RGR for ura3, trp1, and his3 inactivation using CRISPR-Cas9 | |
|---|---|
| Component name | Sequence, 5' to 3' |
| gRNA, URA3 | TAACTCCAGTAATTCCTTGG (SEQ ID No. 38) |
| gRNA, TRP1 | GGTCCATTGGTGAAAGTTTG (SEQ ID No. 39) |
| gRNA, HI53 | ATTGCGATCTCTTTAAAGGG (SEQ ID No. 40) |
| Primer for gRNA construct, 1_URA3_A_fw | CATGGAGTTACTGATGAGTCCGTGAGGACGAAACGA GTAAGCTCGTCTAAC (SEQ ID No. 41) |
| Primer for gRNA construct, 2_URA3_A_fw | AAACGAGTAAGCTCGTCTAACTCCAGTAATTCCTTGG gtttagagctagaaatagcaag (SEQ ID No. 42) |
| Primer for gRNA construct, 1_TRP1_A_fw | CATGTGGACCCTGATGAGTCCGTGAGGACGAAACG AGTAAGCTCGTCGGTC (SEQ ID No. 43) |
| Primer for gRNA construct, 2_TRP1_A_fw | AAACGAGTAAGCTCGTCGGTCCATTGGTGAAAGTTT Ggttttagagctagaaatagcaag (SEQ ID No. 44) |
| Primer for gRNA construct, 1_HIS3_A_fw | CATGCGCAATCTGATGAGTCCGTGAGGACGAAACGA GTAAGCTCGTCATTG (SEQ ID No. 45) |
| Primer for gRNA construct, 2_HIS3_A_fw | AAACGAGTAAGCTCGTCATTGCGATCTCTTTAAAGG Ggttttagagctagaaatagcaag (SEQ ID No. 46) |
| Overlapping primer, 4gRNA_all_fw | Gttttagagctagaaatagcaagttaaaataaggctagtc cgttatcaacttgaaaaagt (SEQ ID No. 47) |

TABLE 5 -continued

Sequences of gRNA, primers, dsDNA oligos and RGR for ura3, trp1, and his3 inactivation using CRISPR-Cas9

| Component name | Sequence, 5' to 3' |
| --- | --- |
| Overlapping primer, 1gRNA_all_rev | CGCCATGCCGAAGCATGTTGCCCAGCCGGCGCCAG CGAGGAGGCTGGGACCATGCCGGCC (SEQ ID No. 48) |
| Overlapping primer, 3gRNA_all_rev | AGGCTGGGACCATGCCGGCCaaaagcaccgactcggtgcca cttttttcaagttgataacg (SEQ ID No. 49) |
| Overlapping primer, 2gRNA_all_rev | AAGCAGTCCAAAGCTGTCCCATTCGCCATGCCGAAG CATGTTGCCCAGCCG (SEQ ID No. 50) |
| gRNA construct: HH ribozyme-URA3gRNA-HDV ribozyme with golden gate fusion sites | CATGGAGTTACTGATGAGTCCGTGAGGACGAAACGA GTAAGCTCGTCTAACTCCAGTAATTCCTTGGgttttagag ctagaaatagcaagttaaaataaggctagtccgttatcaa cttgaaaaagtggcaccgagtcggtgcttttGGCCGGCAT GGTCCCAGCCTCCTCGCTGGCGCCGGCTGGGCAACATGCT TCGGCATGGCGAATGGGACAGCTTTGGACTGCTT (SEQ ID No. 51) |
| gRNA construct: HH ribozyme-TRP1g RNA-HDV ribozyme with golden gate fusion sites | CATGTGGACCCTGATGAGTCCGTGAGGACGAAACG AGTAAGCTCGTCGGTCCATTGGTGAAAGTTTGgttttag agctagaaatagcaagttaaaataaggctagtccgttatc aacttgaaaaagtggcaccgagtcggtgcttttGGCCGGC ATGGTCCCAGCCTCCTCGCTGGCGCCGGCTGGGCAACATG CTTCGGCATGGCGAATGGGACAGCTTTGGACTGCTT (SEQ ID No. 52) |
| gRNA construct: HH ribozyme-HIS3gRNA-HDV ribozyme with golden gatef usion sites | CATGCGCAATCTGATGAGTCCGTGAGGACGAAACGA GTAAGCTCGTCATTGCGATCTCTTTAAAGGGgttttagag ctagaaatagcaagttaaaataaggctagtccgttatcaa cttgaaaaagtggcaccgagtcggtgcttttGGCCGGCAT GGTCCCAGCCTCCTCGCTGGCGCCGGCTGGGCAACATGCT TCGGCATGGCGAATGGGACAGCTTTGGACTGCTT (SEQ ID No. 53) |
| dsDNA oligo with stop codons, for TRP1 inactivation | CTGTTATTAATTTCACAGGTAGTTCTGGTCCATTGGT GAAAGTatagTTGCGcCTTGCAGAGCACAGAGGCCGC AGAATGTGCTCTAGAT (SEQ ID No. 54) |
| dsDNA oligo with stop codons, for HI53 inactivation | AAGCGTATTACAAATGAAACCAAGATTCAGATTGCGA TCTCTTaActAGGtTGGTCCCCTAGCGATAGAGCACTC GATCTTCCCAGAAAA (SEQ ID No. 55) |
| dsDNA oligo with stop codons, for URA3 inactivation | TCATGCACGAAAAGCAAACAAACTTGTGTGCTTCATT GGATGTTCGTACCTAACTAAGTAATTAGTTGAAGCAT TAGGTCCCAAAATTTGTTTACTAAAAACACATGTGGA (SEQ ID No. 56) |

ENGLER, C., KANDZIA, R. & MARILLONNET, S. 2008.
A One Pot, One Step, Precision Cloning Method with High Throughput Capability.
Plos One, 3.

Example 5: Construction of S. cerevisiae (CBS7962 and ΔΔΔpdc) Strains Expressing a Heterologous LDH Activity from Lactobacillus plantarum The S. cerevisiae strain lacking both the alleles of PDC1, PDC5 and PDC6, was transformed with a 2μ plasmid containing LDH gene. As a control, the wild type strain of S. cerevisiae CBS7962 also was transformed with 2μ plasmid containing LDH gene. The region of 2μ contains two 599 bp inverted repeats separated by a large and small unique region; 2μ enables rolling circle replication producing multiple copies of plasmid each cell cycle. The said plasmid was constructed by golden gate assembly procedure (Engler et al., 2008). The LDH gene was previously PCR amplified using the genome of Lactobacillus plantarum ATCC8014 (Branduardi et al., 2006) as a template and primers containing appropriate fusion sites for backbone1 vector. The PCR construct of LDH and a backbone1 linker was BbsI cut to obtain a backbone1 plasmid containing LDH coding sequence. Similarly, backbone1 plasmids containing TPI1 promoter and CYC1 terminator, respectively, were constructed using PCR constructs of respective elements amplified using S. cerevisiae genome as a template. The backbone1 plasmids of LDH, TPI1 promoter and CYC1 terminator, along with a backbone2 linker were BpiI cut to obtain a backbone2 plasmid with a LDH expression cassette. The resulted plasmid along with a backbone3 linker, containing 2μ and an ORI of S. cerevisiae, were BbsI cut to obtain a yeast expression plasmid that was then used for transforming the above mentioned yeast strains. Transformation of both the strains were carried out according to the LiAc/PEG/ss-DNA protocol (http://home.cc.umanitoba.ca/~gietz/method.html). The transformants of ΔΔΔpdc strain was plated on selective YP ethanol-glycerol medium (10 g/l of yeast extract, 20 g/l of peptone, 10 g/l of ethanol and 10 g/l of glycerol). Whereas, the transformants of CBS7962 strain was plated on selective YPD medium (10 g/l of yeast extract, 20 g/l of peptone and 20 g/l of glucose). Single colonies were obtained from both the transformants after 3-4 days of incubation at 30° C.

BRANDUARDI, P., SAUER, M., DE GIOIA, L., ZAMPELLA, G., VALLI, M., MATTANOVICH, D. & PORRO, D. 2006. Lactate production yield from engineered yeasts is dependent from the host background, the lactate dehydrogenase source and the lactate export. *Microbial Cell Factories,* 5.

ENGLER, C., KANDZIA, R. & MARILLONNET, S. 2008. A One Pot, One Step, Precision Cloning Method with High Throughput Capability. *Plos One,* 3.

Example 6: Construction of *S. cerevisiae* CBS7962 Strain with Pyruvate Decarboxylase Genes Under the Control of Conditional Expression System Using CRISPR-Cas9 System The pyruvate decarboxylase genes, PDC1, PDC5 and PDC6 are constitutively expressed in bakers yeast. This example provides a description of disabling constitutive expression of pdc genes and enabling conditional expression of pdcs genes under the control of promoters of either HXT2 gene or HXT4 gene. The genes, HXT2 and HXT4 are expressed at low levels of glucose (0.1%) and repressed at high levels of glucose (Ozcan and Johnston, 1995). Using CRISPR-Cas9 system, the promoters of pdc genes are replaced by the promoter of HXT2 or HXT4 gene. CRISPR-cas9 system, a RNA guided endonuclease activity to induce double stranded DNA breaks (dsb) at the target site and repairing the dsb with double stranded (ds) DNA homology oligos, containing promoter sequence of HXT2 or HXT4, is used to enable conditional expression system of pdc genes. Transformations are carried out according to LiAc/PEG/ss-DNA protocol (http://home.cc.umanitoba.ca/~gietz/method.html). The endonuclease enzyme, cas9, is constructed in a centromeric plasmid under TEF1 promoter and CYC1 terminator using golden gate assembly (Engler et al., 2008). The gRNAs to target the promoters of PDC1, PDC5 and PDC6 are identified using chopchop (https://chopchop.rc.fas.harvard.edu/). The 20 bp gRNAs are constructed to contain a sequence of hammer head (HH) ribozyme and a sequence of hepatitis delta virus (HDV) ribozyme on 5' and 3' ends, respectively. PCR for constructing ribozyme-gRNA-ribozyme (RGR) is performed using four common overlapping primers (Table6) including 1gRNA_all_rev, 2gRNA_all_rev, 3gRNA_all_rev and 4gRNA_all_fw and two forward primers specific for gRNAs of promoters of pdc genes. Using golden gate assembly, the RGR constructs are assembled in a 2µ plasmid with TPI1 promoter and CYC1 terminator. The dsDNA oligos are designed to contain the promoter sequence of HXT2 or HXT4 gene and to both the ends of promoter sequence designed to contain a 40 bp sequence homologous to the regions adjacent to the native promoter of pdc genes. Replacing the constitutive promoters of pdc genes, one promoter at a time, is carried out in two steps. In the first step, a yeast strain expressing cas9 is obtained by transforming the centromeric plasmid, containing cas9, into the yeast strain. The cas9 expressing strain is then transformed with a RGR, containing the gRNA targeting the PDC1 promoter, and dsDNA oligo containing HXT2 or HXT4 promoter sequence. The transformants of CBS792 strain are plated on selective YPDE medium (10 g/l of yeast extract, 20 g/l of peptone, 1 g/l of glucose and 10 g/l of ethanol) and incubated for 3-4 days at 30° C. Single colonies are then subjected to colony PCR using verification primers for the target region. Colony PCR is performed as follows: a yeast colony is gently touched using a pipette tip and transferred to a PCR tube containing 1.2M of sorbitol, 100 mM of sodium hydrogen phosphate and 1500 U/ml of lyticase enzyme and incubated at 37° C. for 15 min; a PCR is performed using verification primers for the target region and the lysed cell suspension as a template. A yeast colony verified to contain HXT2 or HXT4 promoter in the place of PDC1 promoter, is then plated on non-selective medium to get rid of the plasmid containing gRNA of PDC1 promoter. This yeast strain still containing the cas9 expression plasmid is then used to replace the promoters of PDC5 and PDC6, one at a time, with the same procedure described above.

TABLE 6

| Component name | Sequence, 5' to 3' |
|---|---|
| Overlapping primer, 4gRNA_all_fw | Gttttagagctagaaatagcaagttaaaata aggctagtccgttatcaacttgaaaaagt (SEQ ID No. 57) |
| Overlapping primer, 1gRNA_all_rev | CGCCATGCCGAAGCATGTTGCCCAGCCGGCGCCAGC GAGGAGGCTGGGACCATGCCGGCC (SEQ ID No. 58) |
| Overlapping primer, 3gRNA_all_rev | AGGCTGGGACCATGCCGGCCaaaagcaccgactcgg tgccacttttctcaagttgataacg (SEQ ID No. 59) |
| Overlapping primer, 2gRNA_all_rev | AAGCAGTCCAAAGCTGTCCCATTCGCCATGCCGAAG CATGTTGCCCAGCCG (SEQ ID No. 60) |

ENGLER, C., KANDZIA, R. & MARILLONNET, S. 2008. A One Pot, One Step, Precision Cloning Method with High Throughput Capability. Plos One, 3.
OZCAN, S. & JOHNSTON, M. 1995. Three different regulatory mechanisms enable yeast hexose transporter (HXT) genes to be induced by different levels of glucose. Mol Cell Biol, 15, 1564-72.

Example 7: Construction of *S. cerevisiae* (CBS7962 and ΔΔΔpdc) Strain for Deletion of 225 bp Internal Region in MTH1 Gene Using CRISPR-Cas9 System CRISPR-cas9 system, a RNA guided endonuclease activity to induce double stranded DNA breaks (dsb) at the target site and repairing the dsb with double stranded (ds) DNA homology oligos is used to delete a region of 225 bp (169 to 393 bp) (Table 8) in MTH1 gene. Two guide RNAs (gRNA) are used to induce two dsb and a dsDNA oligo, of 500 bp flanking regions of internal deletion sequence, is used to repair the dsb. Transformations are carried out according to LiAc/PEG/ss-DNA protocol (http://home.cc.umanitoba.ca/~gietz/method.html). The endonuclease enzyme, cas9, is constructed in a centromeric plasmid under TEF1 promoter and CYC1 terminator using golden gate assembly (Engler et al., 2008). Two gRNAs (MTH1_A and MTH1_B) (Table 8) which lie within the region of MTH1 to be deleted are identified using chopchop (https://chopchop.rc.fas.harvard.edu/). Similarly two gRNAs (MTH1_C and MTH1_D) outside this region are identified. The 20 bp gRNAs are constructed to contain a sequence of hammer head (HH) ribozyme and a sequence of hepatitis delta virus (HDV) ribozyme on 5' and 3' ends, respectively (Table 8). The ribozyme-gRNA-ribozyme (RGR) construct is obtained using PCR with overlapping primers (Table 8). PCR for constructing RGR is performed using four common overlapping primers including 1gRNA_all_rev, 2gRNA_all_rev, 3gRNA_all_rev and 4gRNA_all_fw and two forward primers specific for MTH1_A and MTH1_B gRNAs (Table 8). Using golden gate assembly, both the RGR constructs are assembled in a 2µ plasmid with TPI1 promoter and CYC1 terminator. The dsDNA oligo, used for assisting the deletion of 225 bp by homologous recombination, is PCR constructed to contain 500 bp homology regions (Table 8) that lie on both sides of internal deletion region. The dsDNA oligo is amplified in a fusion PCR using the genomic DNA of CBS7962 strain with an overlapping primer set (Table 8). Partial in-frame deletion of MTH1 gene is carried out in two steps. In the first step, a yeast strain expressing cas9 is obtained by transforming the centromeric plasmid, containing cas9, into the yeast strains. The cas9 expressing strain is transformed with RGRs of MTH1_A and MTH1_B (or MTH1_C and MTH1_D, respectively) plasmid and the respective dsDNA oligo. The transformants of CBS792 and ΔΔΔpdc strain are plated on selective YPD medium (10 g/l of yeast extract, 20 g/l of peptone and 20 g/l of glucose) and incubated for 3-4 days at 30° C. Single colonies were then subjected to colony PCR using verification primers (Table 8) for the target gene. Colony PCR was performed as follows: a yeast colony was gently touched using a pipette tip and transferred to a PCR tube containing 1.2M of sorbitol, 100 mM of sodium hydrogen phosphate and 1500 U/ml of lyticase enzyme and incubated at 37° C. for 15 min; a PCR was performed using verification primers of the target gene and the lysed cell suspension as a template.

TABLE 7

Sequences of gRNA, primers, dsDNA oligos and RGR for MTH1 internal in-frame deletion using CRISPR-Cas9

| Component name | Sequence, 5' to 3' |
| --- | --- |
| 225 bp (169 to 393 bp) of internal deletion sequence of MTH1 | AGTAGCTCTCAATCCACGACTTCTTCGAGAAGAG AGAACTTTGTGAATGCTCCTCCGGAGTACACTGA TAGAGCTAGAGATGAGATTAAAAAAAGATTATTG GCCTCCTCACCTAGCAGAAGGTCACATCATTCAA GCAGTATGCATTCAGCGAGCAGGAGATCAAGCG TGGCTGAAAGTGGGAGTTTACTTTCGGATAATGC CTCGTCTTATCAATCAAGTATA (SEQ ID No. 61) |
| gRNA, MTH1_a | CTCTCTTCTCGAAGAAGTCG (SEQ ID No. 62) |
| gRNA, MTH1_b | AGATCAAGCGTGGCTGAAAG (SEQ ID No. 63) |
| Primer for gRNA construct, 1_MTH1_A_fw | CATGAGAGAGCTGATGAGTCCGTGAGGACGAAA CGAGTAAGCTCGTCCTCT (SEQ ID No. 64) |
| Primer for gRNA construct, 2_MTH1_A_fw | AAACGAGTAAGCTCGTCCTCTCTTCTCGAAGAAGTCG gttttagagctagaaatagcaag (SEQ ID No. 65) |
| Primer for gRNA construct, 1_MTH1_B_fw | CATGTGATCTCTGATGAGTCCGTGAGGACGAAA CGAGTAAGCTCGTCAGAT (SEQ ID No. 66) |
| Primer for gRNA construct, 2_MTH1_B_fw | AAACGAGTAAGCTCGTCAGATCAAGCGTGGCTGAAAG gttttagagctagaaatagcaag (SEQ ID No. 67) |
| Overlapping primer, 4gRNA_all_fw | Gttttagagctagaaatagcaagttaaaataaggcta gtccgttatcaacttgaaaaagt (SEQ ID No. 68) |
| Overlapping primer, 1gRNA_all_rev | CGCCATGCCGAAGCATGTTGCCCAGCCGGCGC CAGCGAGGAGGCTGGGACCATGCCGGCC (SEQ ID No. 69) |
| Overlapping primer, 3gRNA_all_rev | AGGCTGGGACCATGCCGGCCaaaagcaccgactcggt gccacttttcaagttgataacg (SEQ ID No. 70) |
| Overlapping primer, 2gRNA_all_rev | AAGCAGTCCAAAGCTGTCCCATTCGCCATGCCG AAGCATGTTGCCCAGCCG (SEQ ID No. 71) |
| gRNA construct: HH ribozyme-mthi_a-gRNA-HDV ribozyme with golden gate fusion sites | CATGAGAGAGCTGATGAGTCCGTGAGGACGAAA CGAGTAAGCTCGTCCTCTCTTCTCGAAGAAGTCG gttttagagctagaaatagcaagttaaaataagg ctagtccgttatcaacttgaaaaagtggcaccga gtcggtgcttttGGCCGGCATGGTCCCAGCCTCC TCGCTGGCGCCGGCTGGGCAACATGCTTCGGCA TGGCGAATGGGACAGCTTTGGACTGCTT (SEQ ID No. 72) |
| gRNA construct: HH ribozyme-mthi_b-gRNA-HDV ribozyme with golden gate fusion sites | CATGTGATCTCTGATGAGTCCGTGAGGACGAAA CGAGTAAGCTCGTCAGATCAAGCGTGGCTGAAA Ggttttagagctagaaatagcaagttaaaataa ggctagtccgttatcaacttgaaaaagtggcac cgagtcggtgcttttGGCCGGCATGGTCCCAGC CTCCTCGCTGGCGCCGGCTGGGCAACATGCTTC GGCATGGCGAATGGGACAGCTTTGGACTGCTT (SEQ ID No. 73) |

TABLE 7 -continued

Sequences of gRNA, primers, dsDNA oligos and RGR for MTH1 internal in-frame deletion using CRISPR-Cas9

| Component name | Sequence, 5' to 3' |
| --- | --- |
| First half of dsDNA oligo: 500 bp upstream of internal deletion region of MTH1 | GGAATATCTGCCATTCTACCCCTTATTCAAGTGC CTTTTTTTTTTTTTTTCATCCCACATTTTATTGCTG CCTCAATCTCCATTAAGAAAAAAAATTTATATAAC CAAATGACATTTTTCCTTTCTTCTCAAACTTTGTA ATGCGCCTGTAACTGCTTCTTTTTTTATTAAAAAA CAGCATGGAGTTTTTTAATAACTTAAGGAAACATA CAAAAAGATTTGTTCATTTCACTCCAAGTATTTTT TAAAGTATATTGAAAGTTCTCAATAGCGAAACCA CAAGCAGCAATACAAAGAGAATTTTATTCGAACG CATAGAGTACACACACTCAAAGGAATGTTTGTTT CACCACCACCAGCAACTTCGAAAAACCAAGTTTT ACAACGACGTCCATTAGAATCGACTAACAGTAAT CATGGGTTTGCAAGCTCCCTACAGGCCATTCCG GAAAACACGATGAGTGGCAGTGATAATGCTTCTT TTCAAAGTTTGCCACTATCAAT (SEQ ID No. 74) |
| Second half of dsDNA oligo: 500 bp downstream of internal deletion region of MTH1 | GTTTTCTGCCCCCTCTACTGTGCACACGCAACTA ACTAATGACTCTTCGTTCTCCGAATTTCCTAACCA CAAGTTAATCACGAGAGTGAGCCTGGATGAAGC ATTACCCAAAACGTTTTATGACATGTATTCGCCA GATATTCTATTAGCAGACCCATCCAACATTCTCT GTAACGGGCGTCCCAAGTTTACCAAGAGAGAGT TATTGGATTGGGATTTAAACGATATAAGATCGTTA TTGATAGTCGAGAAGTTAAGGCCCGAATGGGGT AATCAACTACCGGAAGTAATAACGGTGGGTGATA ATATGCCCCAGTTTAGGTTACAATTATTACCACTA TATTCTAGCGATGAGACCATAATCGCAACGTTAG TCCATTCGGATCTGTACATGGAGGCTAACTTAGA TTATGAATTCAAACTAACCAGCGCCAAATATACA GTAGCGACCGCTAGAAAAAGACATGAGCATATAA CTGGTAGAAATGAAGCCGTCAT (SEQ ID No. 75) |
| Amplification primer_fw | GGAATATCTGCCATTCTACC (SEQ ID No. 76) |
| Amplification overlapping primer_rev | GAGGGGGCAGAAAACATTGATAGTGGCAAAC (SEQ ID No. 77) |
| Amplification overlapping primer_rev | GTTTGCCACTATCAATGTTTTCTGCCCCCTC (SEQ ID No. 78) |
| Amplification primer_rev | ATGACGGCTTCATTTCTACC (SEQ ID No. 79) |
| Verification primer_fw | TACGAGTCCATTTCTCCAGT (SEQ ID No. 80) |
| Verification primer_rev | ATTGTGCCTCTACTGCTATA (SEQ ID No. 81) |

Example 8: Construction of S. cerevisiae (CBS7962 and ΔΔΔpdc) Strains to Overexpress an Endogenous MTH1 Gene The S. cerevisiae strain lacking both the alleles of PDC1, PDC5 and PDC6, was transformed with a 2μ plasmid containing MTH1 gene. As a control, the wild type strain of S. cerevisiae CBS7962 also was transformed with 2μ plasmid containing MTH1 gene. The region of 2μ contains two 599 bp inverted repeats separated by a large and small unique region; 2μ enables rolling circle replication producing multiple copies of plasmid each cell cycle. The said plasmid was constructed by golden gate assembly procedure (Engler et al., 2008). The MTH1 gene was previously PCR amplified using the genome of CBS7962 strain as a template and amplification primers (Table 9) containing appropriate fusion sites for backbone1 vector. The PCR construct of MTH1 and a backbone1 linker was BbsI cut to obtain a backbone1 plasmid containing MTH1 coding sequence. Similarly, backbone1 plasmids containing TPI1 promoter and CYC1 terminator, respectively, were constructed using PCR constructs of respective elements amplified using CBS7962 genome as a template. The backbone1 plasmids of MTH1, TPI1 promoter and CYC1 terminator, along with a backbone2 linker were BpiI cut to obtain a backbone2 plasmid with a MTH1 expression cassette. The resulted plasmid along with a backbone3 linker, containing 2μ and an ORI of S. cerevisiae, were BbsI cut to obtain a yeast expression plasmid that was then used for transforming the above mentioned yeast strains. Transformation of both strains was carried out according to the LiAc/PEG/ss-DNA protocol (http://home.cc.umanitoba.ca/~gietz/method.html). The transformants of CBS7962 and ΔΔΔpdc strain were plated on selective YPD medium (10 g/l of yeast extract, 20 g/l of peptone and 20 g/l of glucose). Single colonies were obtained from both the transformants after 3-4 days of incubation at 30° C.

TABLE 8

MTH1 amplification primers

| Component name | Sequence, 5' to 3' |
| --- | --- |
| MTH1_amplification primer_fw | AGAAGACGCTAGCGATGAAACCATAATCGC (SEQ ID No. 82) |

TABLE 8 -continued

MTH1 amplification primers

| Component name | Sequence, 5' to 3' |
|---|---|
| MTH1_amplificaiton primer_rev | GGTTACAATTATTACCACTATATTCTAGCG CGTCTTCT (SEQ ID No. 83) |

ENGLER, C., KANDZIA, R. & MARILLONNET, S. 2008. A One Pot, One Step, Precision Cloning Method with High Throughput Capability. Plos One, 3.

Example 9: Lactic Acid Production Using S. cerevisiae (CBS7962-LDH and ΔΔΔpdc-LDH) Strains The S. cerevisiae CBS7962 strain expressing a heterologous LDH gene from L. plantarum was cultivated in shake flasks in two stages. An inoculum development stage wherein YPD with 20 g/l of glucose was used as a preinoculum medium and a production stage wherein YPD with 250 g/l of glucose was used as a fermentation medium. Batch culture was performed at 30° C. in 100 ml shake flasks. Cells from glycerol vials stored at −80 C were used to inoculate a 20 ml of preinoculum medium at an optical density 600 nm (OD600) of 0.05. After 24 h of growth, the cells were harvested and used to inoculate a 50 ml of fermentation medium at an OD600 of 0.1.

The ΔΔΔpdc strain expressing a heterologous LDH gene was cultivated in shake flasks in two different liquid media. A preinoculum medium containing 1.8 g/l of yeast nitrogen base (YNB) without amino acids and without (NH4)2SO4, 1 g/l of urea, 20 g/l of ethanol and 0.5 g/l of glucose and a fermentation medium containing 4.5 g/l of CaCO3, 1.8 g/l of YNB without amino acids and without (NH4)2SO4, 1 g/l of urea, 1 g/l of ethanol and 40 g/l of glucose, pH 5. Batch culture was performed at 30° C. in 100 ml shake flasks. Cells from glycerol vials stored at −80° C. were used to inoculate a 50 ml of preinoculum medium at an optical density 600 nm (OD600) of 0.1. After 36 h of growth, the cells were harvested and used to inoculate a 50 ml of fermentation medium at an OD600 of 4.5.

The cultures were incubated at 30 C at 180 rpm and samples were collected at frequent intervals to monitor growth by OD600 measurement. The supernatant was analyzed using an Aminex HPX-87H column set in a HPLC (Shimadzu scientific instruments) at 60° C., and 5 mM $H_2SO_4$ as an eluant with a flow rate of 0.6 ml/min, for metabolites including, glucose, ethanol and lactic acid.

After 40 h of incubation, the strain, CBS7962 expressing LDH, consumed 250 g/l of glucose and produced 9.4 g/l of lactic acid with a yield of 0.04 g of lactic acid per g of glucose consumed. Remarkably, a significant increase in lactic acid yield was observed when ΔΔΔpdc strain expressing LDH was used for lactic acid production. Although ΔΔΔpdc strain expressing LDH did not completely consume 40 g/l of glucose after 96 h of incubation, the strain produced 21.3 g/l of lactic acid with a yield of 0.71 g of lactic acid per g of glucose consumed.

Example 10: Two-Step Process for Lactic Acid Production Under Controlled Conditions The production process of lactic acid is followed in a two-step process: first step is the cultivation of yeast cells to high cell densities in a fed-batch process and the second step is a batch process for lactic acid production with high initial inoculum. As shown previously (Example 1) in shake flasks experiments at low pH of 3.0, the fermentation rate and ethanol yield was significantly improved with high initial inoculum in a medium containing lactic acid and high glucose concentration. This suggested that inoculum size plays a significant role in determining the performance of a fermentation.

The first step starts with a batch culture in a medium containing 1.8 g/l of YNB, 5 g/l of (NH4)2SO4 and 20 g/l of glucose. The dissolved oxygen concentration is maintained at 20% by controlling the stirrer speed and aeration rate. The temperature and pH are maintained at optimal values at 30° C. and 5.0, respectively. The batch culture proceeds until complete consumption of glucose and ethanol before a fresh medium is fed into the reactor. The feed-medium contains high concentrations of glucose, 5.4 g/l of YNB and 10 g/l of (NH4)2SO4. Upon exhaustion of ethanol in the batch culture, the feed-medium is fed in to the reactor with a flow rate necessary to maintain the specific growth rate at the critical value which is strain specific and can be determined using prior chemostat cultivations. Maintaining the specific growth rate at the critical value ensures high biomass yield per substrate consumed without forming byproducts such as ethanol and acetate.

The cells are harvested after the fed-batch cultivation and inoculated to high cell densities into the production reactor. The production medium contains high glucose concentration to ensure high lactic acid titers. The medium is supplemented with necessary nutrients to support cellular metabolism at high glucose concentrations. The pH is a crucial factor in determining the fermentation performance and therefore, maintaining the pH at 5.0 by addition of a salt base or addition of CaCO3 into the medium from the beginning can be a preferred option based on the overall economic analysis of the process.

Example 11: Alternative Two-Step Process for Lactic Acid Production

The production process of lactic acid is followed in a two-step process: first step is the cultivation of yeast cells to high cell densities in a fed-batch process and the second step is a batch process for lactic acid production with high initial inoculum.

First Step of Lactic Acid Production:

The medium for the first culture step is prepared according the following tables, glucose is added to a concentration of 25 g/L:

Minimal Medium Salts

| | |
|---|---|
| (NH4)2SO4 | 5.0 g/L |
| KH2PO4 | 3.0 g/L |
| MgSO4·7H2O | 0.5 g/L |
| 1000× vitamin solution | 1 mL/L |
| 100× trace elements | 10 mL/L |

The ingredients are dissolved in $H_2O$, the vitamin solution and the trace elements are added, the pH is adjusted to 5.0 with hydrochloric acid. The medium is sterile filtered.

1000× Vitamin Solution for Minimal Glucose Medium

| | |
|---|---|
| D-biotin | 0.05 g/L |
| Ca-D-pantothenate | 1.00 g/L |
| Nicotonic acid | 1.00 g/L |
| Myo-inositol | 25.00 g/L |

| | |
|---|---|
| Thiamine hydrochloride | 1.00 g/L |
| Pyridoxal hydrochloride | 1.00 g/L |
| p-aminobenzoic acid | 0.20 g/L |

Biotin is dissolved in 0.1 M NaOH and diluted in $H_2O$, then the pH is adjusted to 6.5 with 1 M hydrochloric acid. All other components are added and the solution is sterile filtered.

100× Trace Elements for Minimal Glucose Medium

| | |
|---|---|
| $Na_2EDTA$ | 1.50 g/L |
| $ZnSO_4 \cdot 7H_2O$ | 0.45 g/L |
| $MnCl_2 \cdot 2H_2O$ | 0.10 g/L |
| $CoCl_2 \cdot 6H_2O$ | 0.03 g/L |
| $CuSO_4 \cdot 5H_2O$ | 0.03 g/L |
| $Na_2MoO_4 \cdot 2H_2O$ | 0.04 g/L |
| $CaCl_2 \cdot 2H_2O$ | 0.45 g/L |
| $FeSO_4 \cdot 7H_2O$ | 0.30 g/L |
| $H_3BO_3$ | 0.10 g/L |
| KI | 0.01 g/L |

EDTA and zinc sulfate are dissolved in $H_2O$ and the pH is adjusted with sodium hydroxide to 6.0. All other components are added and the pH is adjusted with hydrochloric acid to 4.0. The solution is sterile filtered.

A batch culture is inoculated in a stirred tank reactor to an optical density of 1 from an overnight pre-culture on YPD medium with washed yeast cells. The dissolved oxygen concentration is maintained at 20% by controlling the stirrer speed and aeration rate. The temperature and pH are maintained at 30° C. and 5.0, respectively. The batch culture proceeds until complete consumption of glucose. When glucose is finished the feed is started. The feed-medium contains 500 g/L of glucose and 2× the medium composition as described above. The feed rate is exponential and corresponds to 80% of the maximal growth rate of the yeast strain. The temperature and pH are maintained at 30° C. and 5.0, respectively. The feed continues to a biomass concentration of 100 g/L.

The second step of the process is initiated by harvest of the cells and inoculation into the production reactor to a concentration of 50 g/L dry cell weight. The production medium contains 150 g/L glucose. The dissolved oxygen concentration is maintained at 20% by controlling the stirrer speed and aeration rate. The temperature is maintained at 30° C. The pH remains uncontrolled and decreases below 3 upon production of lactic acid. The batch culture proceeds until complete consumption of glucose.

An alternative for the second step of the process is the addition of medium to the first reactor to obtain a glucose concentration of 150 g/L and a biomass concentration of 50 g/L. The dissolved oxygen concentration is maintained at 20% by controlling the stirrer speed and aeration rate. The temperature is maintained at 30° C. The pH remains uncontrolled and decreases below 3 upon production of lactic acid. The batch culture proceeds until complete consumption of glucose.

Example 12: Adaptive Laboratory Evolution (ALE) of ΔΔΔpdc S. cerevisiae (CBS7962) Strain Expressing a Heterologous LDH Gene The ΔΔΔpdc S. cerevisiae strain expressing a heterologous LDH gene from L. plantarum (Example 5) was subjected to adaptive laboratory evolution (ALE). The ALE was conducted in 100 mL shake flasks, containing 10 mL medium, by regularly passaging the overnight culture into a fresh liquid fermentation medium until the culture reached 100 generations.

A preinoculum medium and two different fermentation media, depending on the concentration of carbon source, were used: A preinoculum medium containing 3.4 g/L of yeast nitrogen base (YNB) without amino acids and without $(NH4)_2SO_4$, 4.54 g/L of urea and 10 g/L of ethanol was used. The fermentation media containing 3.4 g/L of yeast nitrogen base (YNB) without amino acids and without $(NH4)_2SO_4$, 4.54 g/L of urea, 5 g/L of ethanol and 100 g/L of glucose or 150 g/L of glucose were used, respectively. Four independent evolution experiments for each fermentation medium (100 and 150 g/L glucose) were performed (in total eight).

The non-evolved cells from glycerol vials, stored at −80° C., were used to inoculate 25 mL of preinoculum medium at an optical density 600 nm ($OD^{600}$) of 0.25. After 24 h of growth, the cells were harvested, washed and used for ALE to inoculate 10 mL of fermentation medium at an $OD^{600}$ of 0.5. The ALE experiment was conducted until cultures reached 100 generations which corresponds to approximately 40 transfers. The cultures were incubated at 28° C. at 180 rpm. Growth was monitored daily by $OD^{600}$ measurement. Supernatants were periodically analysed for metabolites using an Aminex HPX-87H column set in a HPLC (Shimadzu scientific instruments) at 60° C., and 5 mM $H_2SO_4$ as a mobile phase with a flow rate of 0.6 mL/min, RID detector, including glucose, ethanol, acetic acid, glycerol and lactic acid.

After 100 generations the evolved strains exhibited an improved growth rate and productivity when compared with non-evolved strain (Table 1). The specific growth rate and the lactic acid concentration in the first 24 h of the non-evolved strain were 0.054 $h^{-1}$ and 2.82 g/L, respectively. After 40 transfers, which correspond to 100 generations, the specific growth rate and the lactic acid concentration in the first 24 h (with starting glucose concentration of 100 g/L) were 0.08 $h^{-1}$ and 5.8 g/L respectively. Improved specific growth rate of the culture after 40 transfers in the fermentation media with 150 g/L of glucose was also detected: μ=0.108 $h^{-1}$ and the lactic acid production was improved from 2.5 g/L to 4.2 g/L. Furthermore, the ethanol concentration during the evolution experiment and after 24 h of incubation, dropped from 2.9 g/L for non-evolved strain to 2.3 g/L for evolved strain after approximately 100 generations.

| | μ ($h^{-1}$) | Lactate (g/L) | Ethanol (g/L) | Time (h) | Number of generations (ALE) |
|---|---|---|---|---|---|
| Non-evolved | 0.054 | 2.82 | 2.9 | 24 | 2 |
| evolved in 100 g/L glucose | 0.08 | 5.8 | 2.3 | 24 | 90 |
| evolved in 150 g/L glucose | 0.1 | 4.2 | 2.2 | 24 | 100 |

Example 13: Characterization of ΔΔΔpdc S. cerevisiae (CBS7962) in a Bioreactor with Partially Controlled pH Value The ΔΔΔpdc S. cerevisiae CBS7962 strain expressing a heterologous LDH gene from L. plantarum was cultivated in a bioreactor in two stages: a first stage for biomass accumulation, wherein 10 g/L of ethanol, 3.4 g/L of yeast nitrogen base (YNB) without amino acids and without (NH4)$_2$SO$_4$ and with 4.54 g/L of urea was used as medium and a production stage wherein 100 g/L of glucose, 5 g/L of ethanol, 3.4 g/L of yeast nitrogen base (YNB) without amino acids and without (NH4)$_2$SO$_4$ and 4.54 g/L of urea was used as a fermentation medium. The first stage was performed in shake flasks and the production stage was performed in a bioreactor (DASGIP system). The shake flask culture was grown at 28° C. in 2000 ml Erlenmeyer flasks, containing 225 mL medium. The cells from the ALE experiments were taken after 50 generations and used to inoculate the first stage at an optical density 600 nm (OD$^{600}$) of 2.5. After 30 h of growth, the cells were harvested, washed with water and used to inoculate 330 ml of fermentation medium at an OD600 of 5 in a 1.5 L bioreactor. The dissolved oxygen concentration was maintained at 30% by controlling stirrer speed and aeration rate. The temperature was maintained at optimal value at 28° C. The pH value was maintained for 18 h at the value of 5 and then was not controlled anymore.

Samples were taken in regular intervals to monitor the growth by OD$^{600}$ and the supernatant was analysed for metabolites using an Aminex HPX-87H column set in a HPLC (Shimadzu scientific instruments) at 60° C., and 5 mM H$_2$SO$_4$ as a mobile phase with a flow rate of 0.6 mL/mi, RID detection, including glucose, ethanol, glycerol, acetic acid and lactic acid. In the first 64 h after stopping the pH control, the pH value decreased from 5 to 3 and then very slightly dropped to a final value of 2.89. The lactic acid production was 30.7 g/L which corresponds to a yield of 0.66 g of lactic acid per g of glucose consumed. Ethanol was consumed in first 40 h after starting batch.

| Time (h) | Glucose consumed (g/L) | Lactate (g/L) | Ethanol (g/L) | Number of generations (ALE) | Yield (g/g) | pH value | OD$^{600}$ |
|---|---|---|---|---|---|---|---|
| 15 | 11.0 | 6.22 | 2.3 | 50 | 0.57 | 5 | 12.9 |
| 64 | 46.8 | 30.7 | — | 50 | 0.66 | 2.99 | 25.3 |

Example 14: Characterization of ΔΔΔpdc S. cerevisiae (CBS7962) in a is Bioreactor without pH Control The ΔΔΔpdc S. cerevisiae CBS7962 strain expressing a heterologous LDH gene from L. plantarum was cultivated in a bioreactor in two stages: a first stage for biomass accumulation, wherein 10 g/L of ethanol, 3.4 g/L of yeast nitrogen base (YNB) without amino acids and without (NH4)$_2$SO$_4$ and with 4.54 g/L of urea was used as medium and a production stage wherein 100 g/L of glucose, 5 g/L of ethanol, 3.4 g/L of yeast nitrogen base (YNB) without amino acids and without (NH4)$_2$SO$_4$ and 4.54 g/L of urea was used as a fermentation medium. The first stage was performed in shake flasks and the production stage was performed in a bioreactor (DASGIP system). The shake flask culture was grown at 28° C. in 2000 ml Erlenmeyer flasks, containing 225 mL medium. The cells from the ALE experiments were taken after 75 generations and used to inoculate the first stage at an optical density 600 nm (OD$^{600}$) of 2.5. After 30 h of growth, the cells were harvested, washed with water and used to inoculate 330 ml of fermentation medium at an OD600 of 5 in a 1.5 L bioreactor. The dissolved oxygen concentration was maintained at 30% by controlling stirrer speed and aeration rate. The temperature was maintained at optimal value at 28° C. The pH value was not controlled at all from the beginning of the fermentation.

Samples were taken in regular intervals to monitor the growth by OD$^{600}$ and the supernatant was analysed for metabolites using an Aminex HPX-87H column set in a HPLC (Shimadzu scientific instruments) at 60° C., and 5 mM H$_2$SO$_4$ as a mobile phase with a flow rate of 0.6 mL/mi, RID detection, including glucose, ethanol, glycerol, acetic acid and lactic acid.

Within the first 15 h of cultivation the pH rapidly dropped from initially 5 to 2.45, and then slightly decreased to remarkable 2.15 after 64 h. During that period, 27.6 g/L of glucose was consumed and 24.5 g/L of lactic acid was produced (which further correspond to a yield of 0.89 g of lactic acid per g of glucose consumed). Ethanol was completely consumed within 47 h.

| Time (h) | Glucose consumed (g/L) | Lactate (g/L) | Ethanol (g/L) | Number of generations (ALE) | Yield (g/g) | pH value | OD$^{600}$ |
|---|---|---|---|---|---|---|---|
| 15 | 7.87 | 6.74 | 2.71 | 75 | 0.86 | 2.45 | 8.6 |
| 64 | 27.6 | 24.5 | — | 75 | 0.89 | 2.16 | 12 |

Example 15: Comparison of Evolved and Non-Evolved ΔΔΔpdc S. cerevisiae Strains (CBS7962) Expressing a Heterologous LDH Gene in Shake Flasks The ΔΔΔpdc S. cerevisiae strain expressing a heterologous LDH gene from L. plantarum was cultivated in shake flasks in two different liquid media. A preinoculum medium containing 3.4 g/L of yeast nitrogen base (YNB) without amino acids and without (NH4)$_2$SO$_4$, 4.54 g/L of urea, 10 g/L of ethanol, and a fermentation medium containing 3.4 g/L of YNB without amino acids and without (NH4)$_2$SO$_4$, 4.54 g/L of urea, 5 g/L of ethanol, 100 g/L of glucose and 4.5 g/L of CaCO$_3$ were used. The batch culture was performed at 28° C. in 500 ml shake flasks, containing 50 mL medium, and with a starting pH value of 6. The non-evolved cells from glycerol vials, stored at −80° C., were used to inoculate 25 ml of preinoculum medium at an optical density 600 nm (OD600) of 1. The cells from the ALE experiment, obtained after 33 transfers and after approximately 75 generations, were used to inoculate 25 ml of preinoculum medium at an optical density 600 nm (OD$^{600}$) of 2. After 40 h of growth, the cells were harvested, washed and used to inoculate a 50 ml of fermentation medium at an OD$^{600}$ of 3.

The cultures were incubated at 28° C. at 180 rpm and samples were collected at frequent intervals (every 24 h) to monitor growth by OD$^{600}$ measurement. The supernatant was analysed for metabolites including, glucose, ethanol, acetic acid, glycerol and lactic acid, using an Aminex HPX-87H column set in a HPLC (Shimadzu scientific instruments) at 60° C., and 5 mM H$_2$SO$_4$ as a mobile phase with a flow rate of 0.6 ml/min and RID detection.

After 48 h of incubation, the non-evolved ΔΔΔpdc strain expressing LDH consumed 14.6 g/L of glucose, while the evolved ΔΔΔpdc strain consumed 32.8 g/L, proving the higher glucose uptake rate of the evolved strain. After 90 h of incubation, the non-evolved strain consumed 23.3 g/L. The evolved strain consumed 59.5 g/L of glucose after 90 h. Ethanol was still present in the culture of the non-evolved strain after 90 h (1.22 g/L), while it was completely consumed by the evolved strain (non detectable by HPLC). The non-evolved strain produced 29.6 g/L of lactic acid and reached a pH value of 3, while the evolved strain finally accumulated 51 g/L of lactic acid at a pH of 2.86. The yield is 86% based on g/g glucose.

| strains | Time (h) | Glucose consumed (g/L) | Lactate (g/L) | Ethanol (g/L) | Number of generations (ALE) | Yield (g/g) | pH value | OD$^{600}$ |
|---|---|---|---|---|---|---|---|---|
| evolved | 48 | 32.8 | 29.3 | 0.31 | 75 | 0.89 | 3.1 | 18.5 |
| evolved | 96 | 59.4 | 51.0 | — | 75 | 0.86 | 2.86 | 18 |

Example 16: Characterization of Evolved ΔΔΔpdc S. cerevisiae Strain (CBS7962) Expressing a Heterologous LDH Gene in Shake Flasks with Different Concentrations of Glucose The ΔΔΔpdc S. cerevisiae strain expressing a heterologous LDH gene from L. plantarum was cultivated in shake flasks. A preinoculum medium and three different fermentation media, with varying concentrations of glucose were used. A preinoculum medium containing 3.4 g/L of yeast nitrogen base (YNB) without amino acids and without $(NH4)_2SO_4$, 4.54 g/L of urea, 10 g/L of ethanol, and a fermentation media containing 3.4 g/L of YNB without amino acids and without $(NH4)_2SO_4$, 4.54 g/L of urea, 5 g/L of ethanol, 4.5 g/L of $CaCO_3$ and 60 g/L of glucose or 70 g/L of glucose or 80 g/L of glucose were used. Batch culture was performed at 28° C. in 500 ml shake flasks, containing 50 mL medium, and with starting pH value 6. The cells from adaptive laboratory evolution (ALE), obtained after 33 transfers (approximately 75 generations) were used to inoculate 25 ml of preinoculum medium at an optical density 600 nm (OD$^{600}$) of 2. After 40 h of growth, the cells were harvested, washed and used to inoculate 50 ml of fermentation medium at an OD$^{600}$ of 3.

The cultures were incubated at 28° C. at 180 rpm and samples were collected at frequent intervals (every 24 h) to monitor growth by OD$^{600}$ measurement. The supernatant was analysed for metabolites including, glucose, ethanol, acetic acid, glycerol and lactic acid, using an Aminex HPX-87H column set in a HPLC (Shimadzu scientific instruments) at 60° C., and 5 mM $H_2SO_4$ as a mobile phase with a flow rate of 0.6 ml/min, and RID detection.

The glucose concentration in all fermentation media decreased during the incubation. After 96 h of incubation, the evolved ΔΔΔpdc strain, expressing LDH and growing on 80 g/L of glucose, converted 55.3 g/L of glucose to 49.4 g/L of lactic acid. This conversion corresponds to the yield of 0.89 g of lactic acid per g of glucose consumed. Due to exhausted glucose after 72 h of incubation in the fermentation media with 60 g/L of glucose, the production of lactic acid reached maximum and remained unchanged thereafter. From the other side, the ethanol concentration in all three fermentation media and after 48 h of incubation was not detected. The growth characteristic (OD$^{600}$ value) and the pH profile during the cultivation were similar for all cultures cultivated in different fermentation media.

| Time (h) | Glucose concentration (g/L) | Glucose consumed (g/L) | Lactate (g/L) | Ethanol (g/L) | Number of generations (ALE) | Yield (g/g) | pH value | OD$^{600}$ |
|---|---|---|---|---|---|---|---|---|
| 48 | 60 | 32.4 | 28.1 | 0.9 | 75 | 0.87 | 3.17 | 10.4 |
| 96 | 60 | 53.1 | 41.7 | — | 75 | 0.79 | 2.98 | 12.5 |
| 48 | 70 | 29.8 | 26.8 | 0.9 | 75 | 0.9 | 3.17 | 10.4 |
| 96 | 70 | 57.4 | 49.2 | — | 75 | 0.86 | 2.85 | 11.5 |
| 48 | 80 | 28.0 | 27.2 | 0.8 | 75 | 0.97 | 3.18 | 10.2 |
| 96 | 80 | 55.3 | 49.4 | — | 75 | 0.89 | 2.84 | 10.8 |

The invention claimed is:

1. A method for producing lactic acid in a recombinant yeast cell culture using glucose as carbon source, comprising:
   a) cultivating an at least diploid yeast in a seed fermentation stage to produce biomass, wherein the yeast is cultivated in a culture medium at a pH of 5 to 7, followed by
   b) cultivating said yeast in a production fermentation stage with biomass from the seed fermentation stage to produce lactic acid, wherein the yeast is inoculated at a cell density of at least an $OD_{600}$ of 5 and cultivated in a culture medium at a pH of <5 until reaching a final pH of <3.5, and
   wherein said yeast is *S. cerevisiae* strain CBS7962 and expresses *Lactobacillus plantarum* lactate dehydrogenase (LDH), wherein said yeast strain has knocked out expression of PDC1, PDC5 and PDC6 genes, and wherein the seed fermentation stage and the production fermentation stage are in separate fermenters.

2. The method according to claim 1, wherein the at least diploid yeast is a polyploid or aneuploid yeast.

3. The method according to claim 1, wherein the production fermentation stage is at a pH of <4.5, <4, or <3.5, and wherein the production fermentation stage has a final pH of 3 or less, <2.9, <2.8, <2.7, <2.6, <2.5, <2.4, <2.3, <2.2, or <2.15.

4. The method according to claim 1, wherein the seed fermentation stage is performed under fed-batch conditions and/or the production fermentation stage is performed under batch process conditions.

5. The method according to claim 1, wherein lactic acid is produced in free form.

6. The method according to claim 1, wherein one or more of promotors of PDC1, PDC5 and/or PDC6 genes are substituted or deleted.

7. The method according to claim 1, wherein at least one of the genes PDC1, PDC5 and/or PDC6 is deleted.

8. The method according to claim 1, wherein the yeast has decreased or knocked-out expression of one or more genes encoding proteins interacting with glucose sensors controlling glucose-regulated gene expression, and wherein the proteins are STD1 or MTH1 proteins.

9. The method according to claim 8, wherein the MTH1 gene is partially or completely deleted.

10. The method of claim 1, wherein the yeast is modified to overexpress at least one hexose transporter gene.

11. The method of claim 1, wherein the yeast is modified to overexpress at least one hexose transporter gene selected from the group consisting of HXT1, HXT2, HXT3, HXT4, HXT5, HXT6, HXT7, HXT8, HXT9, HXT10, HXT11, HXT12, HXT13, HXT14, HXT15, HXT16, HXT17, GAL2, SNF3 and RGT2.

12. A two part fermentation system for producing lactic acid with glucose as carbon source using a recombinant yeast strain, wherein the yeast strain is at least diploid, consisting of:
   a) a seed fermentation stage to produce biomass, wherein the yeast cells are cultivated in a cell culture medium at a pH of 5 to 7, and
   b) a production fermentation stage to produce lactic acid, wherein the yeast cells are cultivated in a cell culture medium until a final pH of less than 3.5, <3.4, <3.3, <3.2, <3.1, <3.0, <2.9, <2.8, <2.7, <2.6, <2.5, <2.4, <2.3, <2.2, or <2.15
   wherein said yeast strain is *S. cerevisiae* strain CBS7962 and expresses *Lactobacillus plantarum* lactate dehydrogenase (LDH) activity, and wherein said yeast strain has knocked out expression of PDC1, PDC5 and PDC6 genes.

13. The system of claim 12, wherein
   the seed fermentation stage is in a first fermenter, and wherein
   the production fermentation stage is in a second fermenter and is inoculated with yeast cells from the seed fermentation stage.

14. The method according to claim 5, wherein the lactic acid is produced in optically pure isomeric form as either D(−) or L(+)-lactic acid.

* * * * *